(12) United States Patent
Katayama et al.

(10) Patent No.: US 10,889,791 B2
(45) Date of Patent: Jan. 12, 2021

(54) COATING AGENT FOR FLOW PASSAGE

(71) Applicant: NISSAN CHEMICAL INDUSTRIES, LTD., Tokyo (JP)

(72) Inventors: Junko Katayama, Tokyo (JP); Yoshiomi Hiroi, Funabashi (JP); Ayako Aihara, Shiraoka (JP); Natsuki Abe, Shiraoka (JP); Taito Nishino, Shiraoka (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/768,427

(22) PCT Filed: Oct. 14, 2016

(86) PCT No.: PCT/JP2016/080547
§ 371 (c)(1),
(2) Date: Apr. 13, 2018

(87) PCT Pub. No.: WO2017/065279
PCT Pub. Date: Apr. 20, 2017

(65) Prior Publication Data
US 2018/0305652 A1    Oct. 25, 2018

(30) Foreign Application Priority Data

Oct. 16, 2015   (JP) .................................. 2015-204397
May 19, 2016    (JP) .................................. 2016-100278

(51) Int. Cl.
*C12M 1/00*      (2006.01)
*C08F 230/02*    (2006.01)
(Continued)

(52) U.S. Cl.
CPC ............ *C12M 23/20* (2013.01); *A61K 35/19* (2013.01); *B01J 19/00* (2013.01); *C08F 220/34* (2013.01);
(Continued)

(58) Field of Classification Search
CPC ......... C08F 120/18; C12M 1/34; C12M 23/20
See application file for complete search history.

(56) References Cited

U.S. PATENT DOCUMENTS

2008/0045686 A1 *  2/2008  Meagher ................. C08J 7/123
                                                    526/329.7
2014/0147879 A1 *  5/2014  Wakamoto ............. C12Q 1/045
                                                    435/29
(Continued)

FOREIGN PATENT DOCUMENTS

CN    105307698 A    2/2016
JP    H05-156204 A   6/1993
(Continued)

OTHER PUBLICATIONS

Japanese Patent Office, International Search Report in International Patent Application No. PCT/JP2016/080547 (dated Nov. 22, 2016).
(Continued)

*Primary Examiner* — Dah-Wei D. Yuan
*Assistant Examiner* — Andrew J Bowman
(74) *Attorney, Agent, or Firm* — Leydig, Voit & Mayer, Ltd.

(57) ABSTRACT

The invention provides a coating agent for a flow passage which comprises a copolymer containing a recurring unit which contains an organic group of the formula (a)
(Continued)

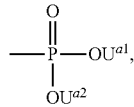

(a)

wherein $U^{a1}$ and $U^{a2}$ are defined herein, and a recurring unit which contains an organic group of the formula (b)

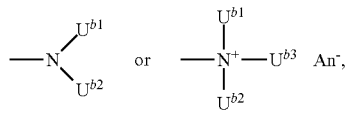

(b)

wherein $U^{b1}$, $U^{b2}$, $U^{b3}$, and $An^-$ are defined herein. The invention also provides a flow passage device having the coating agent for a flow passage on at least part of an inner surface of a flow passage, a platelet-producing flow passage device and a method for manufacturing the same.

18 Claims, 6 Drawing Sheets

(51) Int. Cl.
| | |
|---|---|
| *C09D 143/02* | (2006.01) |
| *G01N 37/00* | (2006.01) |
| *A61K 35/19* | (2015.01) |
| *C12M 1/26* | (2006.01) |
| *B01J 19/00* | (2006.01) |
| *C09D 5/16* | (2006.01) |
| *C09D 201/06* | (2006.01) |
| *C08F 220/34* | (2006.01) |
| *C12M 3/06* | (2006.01) |

(52) U.S. Cl.
CPC .............. *C08F 230/02* (2013.01); *C09D 5/16* (2013.01); *C09D 143/02* (2013.01); *C09D 201/06* (2013.01); *C12M 1/00* (2013.01); *C12M 1/26* (2013.01); *C12M 23/16* (2013.01); *G01N 37/00* (2013.01)

(56) References Cited

U.S. PATENT DOCUMENTS

| | | |
|---|---|---|
| 2015/0017221 A1 | 1/2015 | Hayashi et al. |
| 2016/0115435 A1 | 4/2016 | Otani et al. |
| 2016/0122576 A1 | 5/2016 | Hiroi et al. |
| 2016/0129176 A1 | 5/2016 | Kanaki et al. |
| 2016/0168294 A1 | 6/2016 | Hayashi et al. |

FOREIGN PATENT DOCUMENTS

| | | |
|---|---|---|
| JP | 2002-005887 A | 1/2002 |
| JP | 2006-084393 A | 3/2006 |
| JP | 2007-063459 A | 3/2007 |
| JP | 2010-236955 A | 10/2010 |
| JP | 2014-155471 A | 8/2014 |
| WO | WO 2013/099901 A1 | 7/2013 |
| WO | WO 2014/196650 A1 | 12/2014 |
| WO | WO 2014/196652 A1 | 12/2014 |

OTHER PUBLICATIONS

European Patent Office, Supplementary European Search Report in European Patent Application No. 16855532.4 (dated Sep. 28, 2018).
European Patent Office, Communication Pursuant to Article 94(3) EPC in European Patent Application No. 16855532.4 (dated Oct. 11, 2018).
China National Intellectual Property Office, The First Office Action in Chinese Patent Application No. 201680059049.1 (dated Dec. 27, 2019).

* cited by examiner

COATING AGENT FOR FLOW PASSAGE

CROSS-REFERENCE TO RELATED APPLICATIONS

This patent application is the U.S. national phase of International Patent Application No. PCT/JP2016/080547, filed Oct. 14, 2016, which claims the benefit of Japanese Patent Application No. 2015-204397, filed on Oct. 16, 2015, and Japanese Patent Application No. 2016-100278, filed on May 19, 2016 which are incorporated by reference in their entireties herein.

TECHNICAL FIELD

The present invention relates to a coating agent for a flow passage, and a flow passage device having the coating agent for a flow passage on at least part of the inner surface of the flow passage, a platelet-producing flow passage device and a method for manufacturing the same.

BACKGROUND ART

In recent years, various devices have been developed in which flow passages or holes having predetermined shapes on the order of μm on a substrate (chip) are made by using fine processing technology such as MEMS (Microelectromechanical Systems) technology, etc., and have been used for experiments with a minute amount, or isolation, purification, analysis, etc., in biotechnology and chemical engineering.

Platelets can be produced, for example, by using a bioreactor having a structure similar to that of the human spinal cord. As such a bioreactor, there has been reported a platelet-producing flow passage device which comprises a porous thin film in which a plurality of micropores are formed in a controlled shape and are arranged on a surface on one side thereof, a culture chamber provided on the one side of the porous thin film and the megakaryocytes are cultured, and a microflow passage provided on the other side of the porous thin film and through which a culture medium flows during the megakaryocytes are cultured in the culture chamber (for example, see Patent document 1). Such a reactor can produce platelets by applying shear stress to the megakaryocytes through the micropores.

In a device using a biological sample, however, there are problems that adhesion occurs due to cells or proteins derived from a biological sample on the surface of the device, resulting in clogging and deterioration in accuracy and sensitivity of analysis. In order to solve the problem, there has been reported a microflow passage device coated with a cell adhesion inhibitor containing a polymer having a recurring unit which has a sulfinyl group at a side chain as an effective ingredient (for example, see Patent document 2).

PRIOR ART DOCUMENTS

Patent Documents

Patent Document 1: JP 2014-155471A
Patent Document 2: WO 2013/099901

SUMMARY OF THE INVENTION

Problems to be Solved by the Invention

For the substrate material of the flow passage device, various materials such as glass, a metal-containing compound or a semimetal-containing compound, activated charcoal or a resin, etc., have been used depending on the purpose, and a coating agent capable of being coated on the surface of these materials with a simple and easy operation, and having an excellent ability to inhibit adhesion of a biological substance has still been required. In particular, it is desirable for the flow passage device to apply a desired coating to the inner surface of the flow passage depending on its purpose after forming the flow passage, but such a coating agent has not yet been reported.

Accordingly, an object of the present invention is to provide a coating agent for a flow passage capable of being coated on the inner surface of the flow passage with an extremely simple and easy operation and having an excellent ability to inhibit adhesion of a biological substance, and a flow passage device having the coating agent for a flow passage at least part of the inner surface of the flow passage, a platelet-producing flow passage device and a method for manufacturing the same.

Means to Solve the Problems

The present inventors have found that a polymer having a function of inhibiting adhesion to the biological substances, particularly a copolymer containing a specific anion structure and a specific cation structure, is capable of being coated on the inner surface of the flow passage with an extremely simple and easy operation and having an excellent ability to inhibit adhesion of a biological substance, whereby they have accomplished the present invention.

The present invention is as follows:

[1] A coating agent for a flow passage which comprises a copolymer containing a recurring unit which contains an organic group of the following formula (a) and a recurring unit which contains an organic group of the following formula (b):

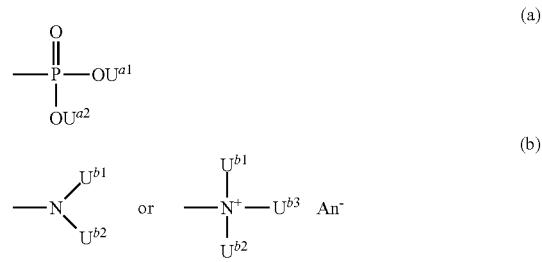

wherein
$U^{a1}$, $U^{a2}$, $U^{b1}$, $U^{b2}$ and $U^{b3}$ each independently represent a hydrogen atom or a linear or branched alkyl group having 1 to 5 carbon atoms, An$^-$ represents an anion selected from the group consisting of a halide ion, an inorganic acid ion, a hydroxide ion and an isothiocyanate ion.

[2] The coating agent for a flow passage described in the above-mentioned [1], wherein the copolymer further comprises a recurring unit which contains an organic group of the following formula (c):

wherein
$R^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, in which the aryl portion may be substituted by a linear or branched alkyl group having 1 to 5 carbon atoms which may be substituted by a halogen atom.

[3] The coating agent for a flow passage described in the above-mentioned [1], wherein the copolymer comprises recurring units of the following formulae (a1) and (b1):

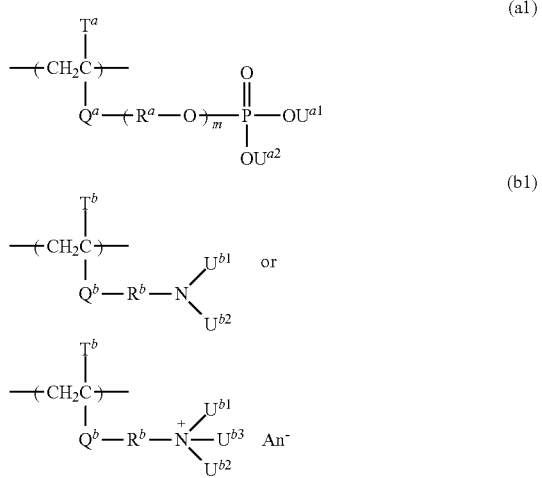

wherein
$T^a$ and $T^b$ each independently represent a hydrogen atom or a linear or branched alkyl group having 1 to 5 carbon atoms;
$Q^a$ and $Q^b$ each independently represent a single bond, an ester bond or an amide bond;
$R^a$ and $R^b$ each independently represent a linear or branched alkylene group having 1 to 10 carbon atoms which may be substituted by a halogen atom;
$U^{a1}$, $U^{a2}$, $U^{b1}$, $U^{b2}$ and $U^{b3}$ each independently represent a hydrogen atom or a linear or branched alkyl group having 1 to 5 carbon atoms;
$An^-$ represents an anion selected from the group consisting of a halide ion, an inorganic acid ion, a hydroxide ion and an isothiocyanate ion; and m represents an integer of 0 to 6.

[4] The coating agent for a flow passage described in the above-mentioned [2], wherein the copolymer further comprises a recurring unit of the following formula (c1):

wherein
$T^c$ each independently represents a hydrogen atom or a linear or branched alkyl group having 1 to 5 carbon atoms;
$Q^c$ represents a single bond, an ether bond or an ester bond; and
$R^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, in which the aryl portion may be substituted by a linear or branched alkyl group having 1 to 5 carbon atoms which may be substituted by a halogen atom.

[5] A flow passage device having the coating agent for a flow passage described in any one of the above [1] to [4] on at least part of an inner surface of a flow passage.

[6] A platelet-producing flow passage device having the coating agent for a flow passage described in any one of the above [1] to [4] on at least part of an inner surface of a flow passage.

[7] A method for manufacturing a flow passage device having a coating agent for a flow passage on at least part of an inner surface of a flow passage, which comprises a process of contacting the coating agent for a flow passage described in any one of the above [1] to [4] with at least part of an inner surface of the flow passage.

[8] A method for manufacturing a platelet-producing flow passage device having a coating agent for a flow passage on at least part of an inner surface of a flow passage, which comprises a process of contacting the coating agent for a flow passage described in any one of the above [1] to [4] with at least part of an inner surface of the flow passage.

[9] A method for manufacturing a flow passage device having a coating agent for a flow passage on at least part of an inner surface of a flow passage, which comprises a process of contacting a coating agent for a flow passage having an ability to inhibit adhesion of a biological substance with at least part of an inner surface of the flow passage after forming the flow passage.

Effects of the Invention

The coating agent for a flow passage of the present invention contains a polymer having an ability to inhibit adhesion of a biological substance, in particular, a copolymer containing a specific anion structure and a specific cation structure, having an excellent ability to inhibit adhesion of a biological substance, and which is capable of being applied to a coating with an extremely simple and easy operation onto various kinds of materials such as glass, a metal-containing compound or a semimetal-containing compound, activated charcoal or a resin, etc. In addition, by optionally introducing a hydrophobic group into the copolymer, a coating having good adhesiveness to a resin such as a plastic and more excellent in durability to an aqueous solvent after fixation can be provided. The coating agent for a flow passage of the present invention can form a coating to an inner surface of a flow passage by contacting it with at least part of an inner surface of a flow passage device, in particular, by an extremely simple and easy operation of feeding the liquid of the coating agent for a flow passage to the flow passage of the flow passage device, so that it is useful in the point that a desired coating can be applied to a flow passage of the flow passage device after forming the flow passage.

EMBODIMENTS TO CARRY OUT THE INVENTION

<<Explanation of the Terms>>

Figure 1A:
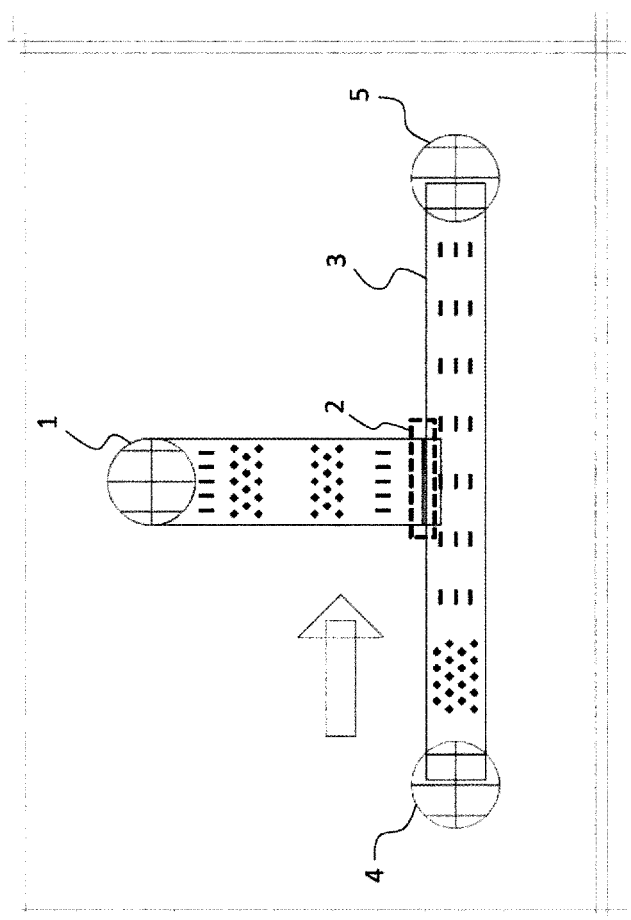
FIG. 1A is a schematic drawing (a figure viewed from the top) of a platelet-producing flow passage device used in Example 1. Megakaryocytes introduced from an introducing part 1 produce platelets at a main filter part 2 portion by a shear force of a culture medium which flows in the direction of an arrow of a flow passage part 3, i.e., flows at a constant flow velocity from a culture medium introducing part 4 to a recovery part 5, whereby the platelets can be recovered more efficiently from the recovery part 5.
Figure 1B:
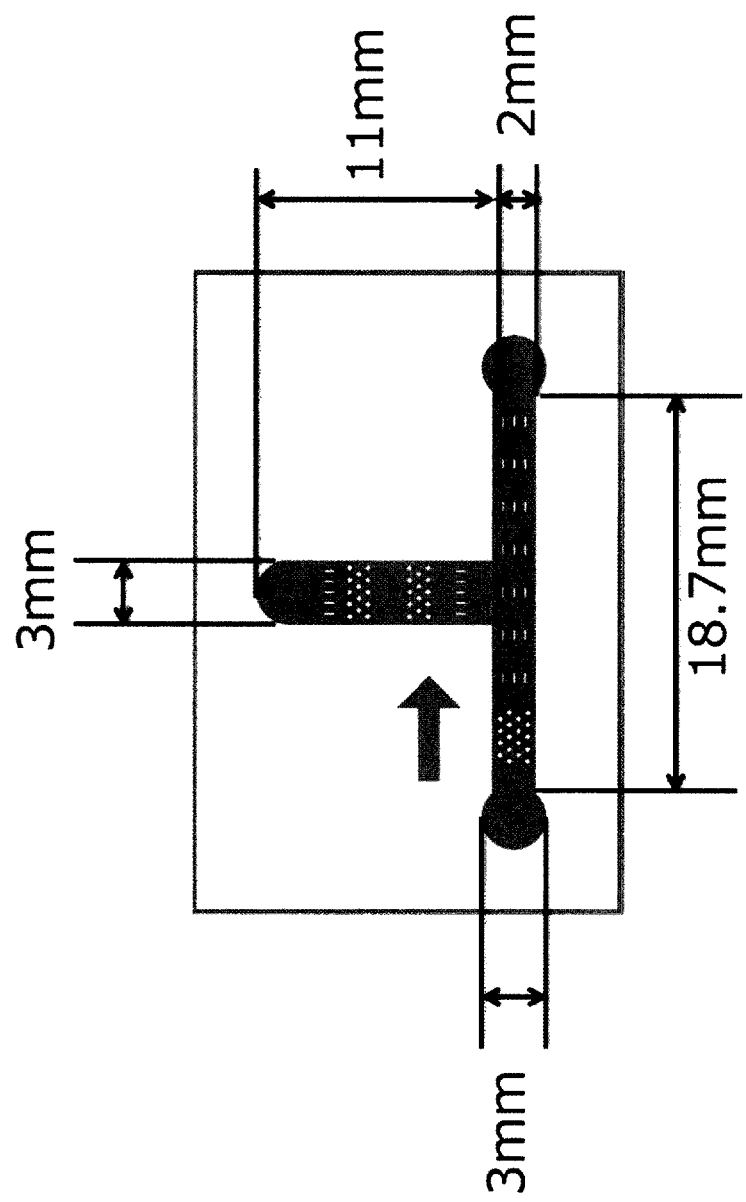
FIG. 1B is a schematic drawing (a figure viewed from the top) of the platelet-producing flow passage device used in Example 1. This is a flow passage device formed by laminating flow passages formed by processing polydimethylsiloxane (PDMS) on a glass plate, and the filled portion is a flow passage.
Figure 1C:
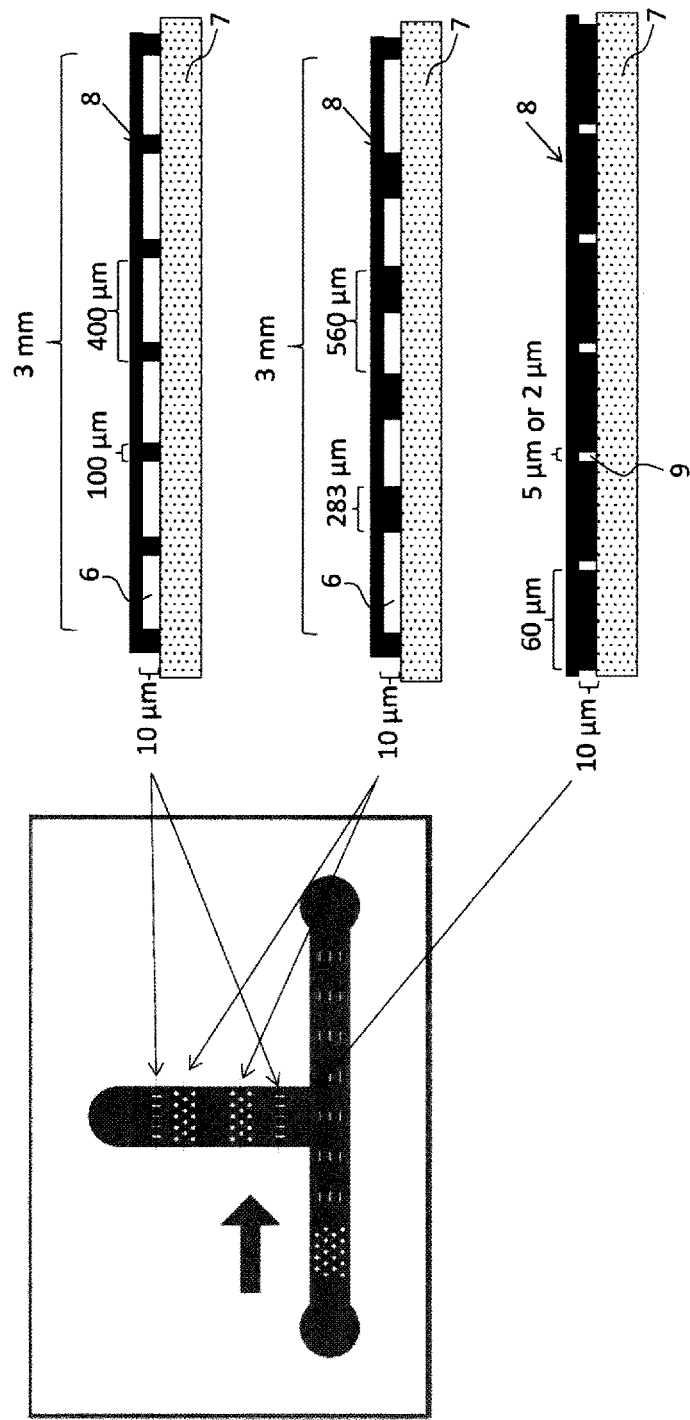
FIG. 1C is a cross-sectional view of the platelet-producing flow passage device used in Example 1.
Figure 1D:
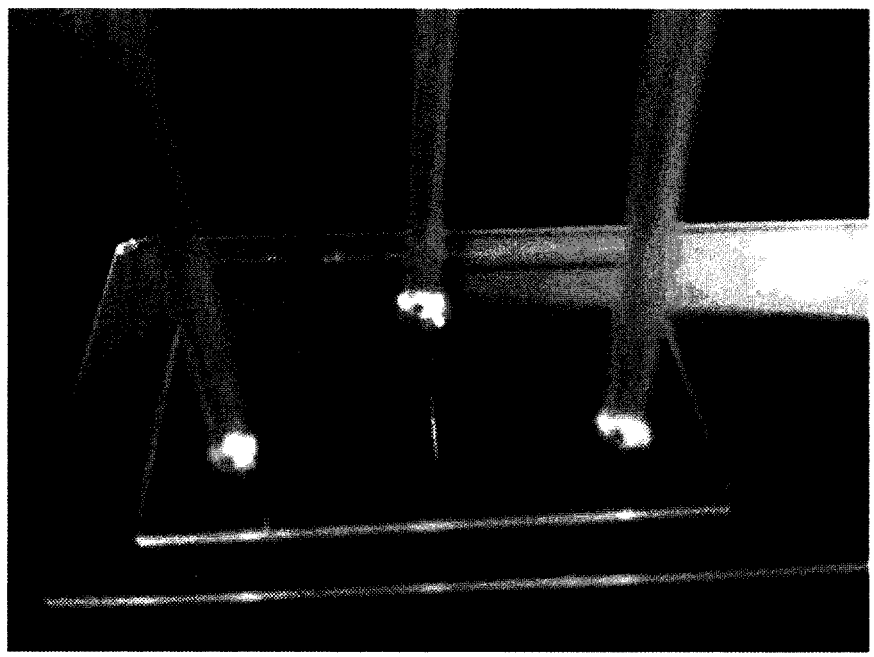
FIG. 1D is a photograph (a photograph taken from the top) of the platelet-producing flow passage device used in Example 1.

The terms used in the present invention have the following definitions, otherwise specifically mentioned.

In the present invention, the "halogen atom" means a fluorine atom, a chlorine atom, a bromine atom or an iodine atom.

In the present invention, the "alkyl group" means a monovalent group of linear or branched, saturated aliphatic hydrocarbon. The "linear or branched alkyl group having 1 to 5 carbon atoms" may be mentioned, for example, a methyl group, an ethyl group, an n-propyl group, an isopropyl group, an n-butyl group, an isobutyl group, an s-butyl group, a t-butyl group, an n-pentyl group, a 1-methylbutyl group, a 2-methylbutyl group, a 3-methylbutyl group, a 1,1-dimethylpropyl group, a 1,2-dimethylpropyl group, a 2,2-dimethylpropyl group or a 1-ethylpropyl group. The "linear or branched alkyl group having 1 to 18 carbon atoms" may be mentioned, in addition to the examples of the "linear or branched alkyl group having 1 to 5 carbon atoms", a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group or an octadecyl group, or an isomer thereof. Similarly, the "linear or branched alkyl group having 1 to 10 carbon atoms" may be mentioned, in addition to the examples of the "linear or branched alkyl group having 1 to 5 carbon atoms", a hexyl group, a heptyl group, an octyl group, a nonyl group, a decyl group, or an isomer thereof.

In the present invention, the "linear or branched alkyl group having 1 to 5 carbon atoms which may be substituted by a halogen atom" means either the linear or branched alkyl group having 1 to 5 carbon atoms, or the linear or branched alkyl group having 1 to 5 carbon atoms substituted by one or more halogen atoms as mentioned above. Examples of the "linear or branched alkyl group having 1 to 5 carbon atoms" are as mentioned above. On the other hand, the "linear or branched alkyl group having 1 to 5 carbon atoms substituted by one or more halogen atoms" means a group in which at least one optional hydrogen atom of the linear or branched alkyl group having 1 to 5 carbon atoms is substituted by a halogen atom, and examples thereof may include a fluoromethyl group, a difluoromethyl group, a trifluoromethyl group, a chloromethyl group, a dichloromethyl group, a trichloromethyl group, a bromomethyl group, an iodomethyl group, a 2,2,2-trifluoroethyl group, a 2,2,2-trichloroethyl group, a perfluoroethyl group, a perfluorobutyl group or a perfluoropentyl group, etc.

In the present invention, the "ester bond" means —C(=O)—O— or —O—C(=O)—, the "amide bond" means —NHC(=O)— or —C(=O)NH— and the "ether bond" means —O—.

In the present invention, the "linear or branched alkylene group having 1 to 10 carbon atoms which may be substituted by a halogen atom" means a linear or branched alkylene group having 1 to 10 carbon atoms or a linear or branched alkylene group having 1 to 10 carbon atoms substituted by one or more halogen atoms. Here, the "alkylene group" means a divalent organic group corresponding to the alkyl group. Examples of the "linear or branched alkylene group having 1 to 10 carbon atoms" may include a methylene group, an ethylene group, a propylene group, a trimethylene group, a tetramethylene group, a 1-methylpropylene group, a 2-methylpropylene group, a dimethylethylene group, an ethylethylene group, a pentamethylene group, a 1-methyl-tetramethylene group, a 2-methyl-tetramethylene group, a 1,1-dimethyl-trimethylene group, a 1,2-dimethyl-trimethylene group, a 2,2-dimethyl-trimethylene group, a 1-ethyl-trimethylene group, a hexamethylene group, an octamethylene group and a decamethylene group, etc., among these, an ethylene group, a propylene group, an octamethylene group and a decamethylene group are preferred, and, for example, a linear or branched alkylene group having 1 to 5 carbon atoms such as an ethylene group, a propylene group, a trimethylene group, a tetramethylene group, etc., are more preferred, and, in particular, an ethylene group or a propylene group is preferred. The "linear or branched alkylene group having 1 to 10 carbon atoms substituted by one or more halogen atoms" means a group in which at least one optional hydrogen atom of the alkylene group is substituted by a halogen atom, or, in particular, a part or whole of the hydrogen atoms of the ethylene group or the propylene group are substituted by a halogen atom(s) is preferred.

In the present invention, the "cyclic hydrocarbyl group having 3 to 10 carbon atoms" means a monovalent group of monocyclic or polycyclic, saturated or partially unsaturated, aliphatic hydrocarbon having 3 to 10 carbon atoms. Among these, a monovalent group of monocyclic or bicyclic, saturated aliphatic hydrocarbon having 3 to 10 carbon atoms is preferred, and there may be mentioned, for example, a cycloalkyl group having 3 to 10 carbon atoms such as a cyclopropyl group, a cyclobutyl group and a cyclohexyl group, etc., or a bicycloalkyl group having 4 to 10 carbon atoms such as a bicyclo[3.2.1]octyl group, a bornyl group and an isobornyl group, etc.

In the present invention, the "aryl group having 6 to 10 carbon atoms" means a monovalent group of monocyclic or polycyclic, aromatic hydrocarbon having 6 to 10 carbon atoms, and there may be mentioned, for example, a phenyl group, a naphthyl group or an anthryl group, etc. The "aryl group having 6 to 10 carbon atoms" may be substituted by one or more of the "linear or branched alkyl group having 1 to 5 carbon atoms which may be substituted by a halogen atom."

In the present invention, the "aralkyl group having 7 to 15 carbon atoms" means a group —R—R', wherein R represents the "alkylene group having 1 to 5 carbon atoms", and R' represents the "aryl group having 6 to 10 carbon atoms", and there may be mentioned, for example, a benzyl group, a phenethyl group or an α-methylbenzyl group, etc. The aryl portion of the "aralkyl group having 7 to 15 carbon atoms" may be substituted by one or more of the "linear or branched alkyl group having 1 to 5 carbon atoms which may be substituted by a halogen atom."

In the present invention, the "aryloxyalkyl group having 7 to 15 carbon atoms" means a group —R—O—R', wherein R represents the "alkylene group having 1 to 5 carbon atoms", and R' represents the "aryl group having 6 to 10 carbon atoms", and there may be mentioned, for example, a phenoxymethyl group, a phenoxyethyl group or a phenoxypropyl group, etc. The aryl portion of the "aryloxyalkyl group having 7 to 15 carbon atoms" may be substituted by one or more of the "linear or branched alkyl group having 1 to 5 carbon atoms which may be substituted by a halogen atom."

In the present invention, "a halide ion" means a fluoride ion, a chloride ion, a bromide ion or an iodide ion.

In the present invention, "an inorganic acid ion" means a carbonate ion, a sulfate ion, a phosphate ion, a hydrogen phosphate ion, a dihydrogen phosphate ion, a nitrate ion, a perchlorate ion or a borate ion.

As the $An^-$, preferred are a halide ion, a sulfate ion, a phosphate ion, a hydroxide ion and an isothiocyanate ion, and particularly preferred is a halide ion.

In the present invention, the (meth)acrylate compound means both of an acrylate compound and a methacrylate compound. For example, the (meth)acrylic acid means acrylic acid and methacrylic acid.

In the present invention, the biological substance may be mentioned a protein, a saccharide, a nucleic acid and a cell or a combination thereof. The protein may be mentioned, for example, fibrinogen, bovine serum albumin (BSA), human albumin, various kinds of globulins, β-lipoprotein, various kinds of antibodies (IgG, IgA, IgM), peroxidase, various kinds of complements, various kinds of lectins, fibronectin, lysozyme, von Willebrand factor (vWF), serum γ-globulin, pepsin, ovalbumin, insulin, histone, ribonuclease, collagen and cytochrome c, the saccharide may be mentioned, for example, glucose, galactose, mannose, fructose, heparin and hyaluronic acid, the nucleic acid may be mentioned, for example, deoxyribonucleic acid (DNA) and ribonucleic acid (RNA), the cell may be mentioned, for example, fibroblast, bone marrow cells, B lymphocytes, T lymphocytes, neutrophils, red blood cells, platelets, macrophages, monocytes, bone cells, bone marrow cells, pericytes, dendritic cells, keratinocytes, fat cells, mesenchymal cells, epithelial cells, epidermal cells, endothelial cells, vascular endothelial cells, hepatic parenchymal cells, cartilage cells, cumulus cells, neural cells, glial cells, neurons, oligodendrocytes, microglia, astroglial cells, heart cells, esophagus cells, muscle cells (for example, smooth muscle cells or skeletal muscle cells), pancreatic beta cells, melanocytes, hematopoietic precursor cells, mononuclear cells, embryonic stem cells (ES cell), embryonic tumor cells, embryonic germline stem cells, induced pluripotent stem cells (iPS cell), neural stem cells, hematopoietic stem cells, mesenchymal stem cells, liver stem cells, pancreatic stem cells, muscle stem cells, germline stem cells, intestinal stem cells, cancer stem cells, hair follicle stem cells, megakaryocytes, CD34 positive spinal cord derived megakaryocytes and various kinds of cell lines (for example, HCT116, Huh7, HEK293 (human embryonic kidney cell), HeLa (human cervical cancer cell lines), HepG2 (human liver cancer cell lines), UT7/TPO (human leukemia cell lines), CHO (Chinese hamster ovary cell lines), MDCK, MDBK, BHK, C-33A, HT-29, AE-1, 3D9, Ns0/1, Jurkat, NIH3T3, PC12, S2, Sf9, Sf21, High Five, Vero), etc., and the coating film of the present invention has a high function of inhibiting adhesion particularly to a serum in which platelets, a protein and a saccharide are mixed, and megakaryocytes (in particular, CD34 positive spinal cord derived megakaryocytes), and in particular, it has a particularly high function of inhibiting adhesion to megakaryocytes (in particular, CD34 positive spinal cord derived megakaryocytes).

<<Explanation of the Present Invention>>

The coating agent for a flow passage of the present invention is not particularly limited as long as it contains a polymer having a function of inhibiting adhesion to the biological substances.

In the present specification, examples of the polymer having the polymer having a function of inhibiting adhesion to the biological substances may include a polymer derived from ethylenically unsaturated monomers, or a polysaccharide or a derivative thereof. Examples of the polymer derived from ethylenically unsaturated monomers may include a polymer derived from one kind or two or more kinds of ethylenically unsaturated monomers selected from the group consisting of a (meth)acrylic acid and an ester thereof; vinyl acetate; vinyl pyrrolidone; ethylene; vinyl alcohol; and these hydrophilic functional derivatives. Examples of the polysaccharide or a derivative thereof may include a cellulose-based polymer such as hydroxyalkyl cellulose (for example, hydroxyethyl cellulose or hydroxypropyl cellulose), etc., starch, dextran and curdlan.

Examples of the hydrophilic functional group of the hydrophilic functional derivatives may include phosphoric acid, phosphonic acid and an ester structure thereof; a betaine structure; an amide structure; an alkylene glycol residue; an amino group; and a sulfinyl group, etc.

Here, phosphoric acid and an ester structure thereof mean a group of the following formula:

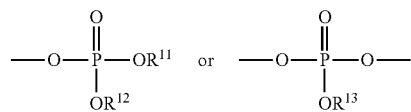

wherein $R^{11}$, $R^{12}$ and $R^{13}$ each independently represent a hydrogen atom or an organic group (for example, a linear or branched alkyl group having 1 to 5 carbon atoms, etc.), and phosphonic acid and an ester structure thereof mean a group of the following formula:

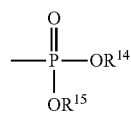

wherein $R^{14}$ and $R^{15}$ each independently represent a hydrogen atom or an organic group (for example, a linear or branched alkyl group having 1 to 5 carbon atoms, etc.). Examples of the ethylenically unsaturated monomer having such a structure may include acid phosphoxyethyl (meth) acrylate and vinylphosphonic acid, etc.

The betaine structure means a monovalent or divalent group of a compound having an amphoteric center of a quaternary ammonium type cation structure and an acidic anion structure, and may be mentioned, for example, a phosphorylcholine group:

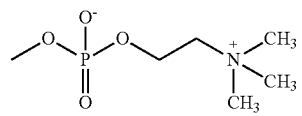

Examples of the ethylenically unsaturated monomer having such a structure may include 2-methacryloyloxyethyl phosphorylcholine (MPC), etc.

The amide structure means a group of the following formula:

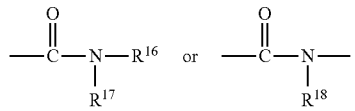

wherein $R^{16}$, $R^{17}$ and $R^{18}$ each independently represent a hydrogen atom or an organic group (for example, a methyl group, a hydroxymethyl group or a hydroxyethyl group, etc.).

Examples of the ethylenically unsaturated monomer having such a structure may include (meth)acrylamide and N-(hydroxymethyl) (meth)acrylamide, etc. In addition, the monomer or polymer having such a structure is disclosed in, for example, JP 2010-169604A, etc.

The alkylene glycol residue means an alkyleneoxy group (-Alk-O—) which remains after a hydroxyl group at one side terminal or both side terminals of alkylene glycol (HO-Alk-OH; wherein, Alk represents an alkylene group having 1 to 10 carbon atoms) is subjected to condensation reaction with the other compound, and also include a poly(alkyleneoxy) group in which an alkyleneoxy unit is repeated. Examples of the ethylenically unsaturated monomer having such a structure may include 2-hydroxyethyl (meth)acrylate and methoxypolyethylene glycol (meth)acrylate, etc. In addition, the monomer or polymer having such a structure is disclosed in, for example, JP 2008-533489 A, etc.

The amino group means a group of the formula: —$NH_2$, —$NHR^{19}$ or —$NR^{20}R^{21}$, wherein $R^{19}$, $R^{20}$ and $R^{21}$ each independently represent an organic group (for example, a linear or branched alkyl group having 1 to 5 carbon atoms, etc.). In the amino group in the present specification, an amino group which is quaternized or chlorinated is included. Examples of the ethylenically unsaturated monomer having such a structure may include dimethylaminoethyl (meth)acrylate, 2-(t-butylamino)ethyl (meth)acrylate and methacryloylcholine chloride, etc.

The sulfinyl group means a group of the following formula:

wherein $R^{22}$ represents an organic group (for example, an organic group having 1 to 10 carbon atoms, preferably an alkyl group having 1 to 10 carbon atoms and having one or more hydroxyl groups, etc.).

The polymer having such a structure may be mentioned a copolymer disclosed in JP 2014-48278A, etc.

Among these, preferred is the coating agent for a flow passage containing the copolymer comprising a recurring unit which contains an organic group of the following formula (a) and a recurring unit which contains an organic group of the following formula (b):

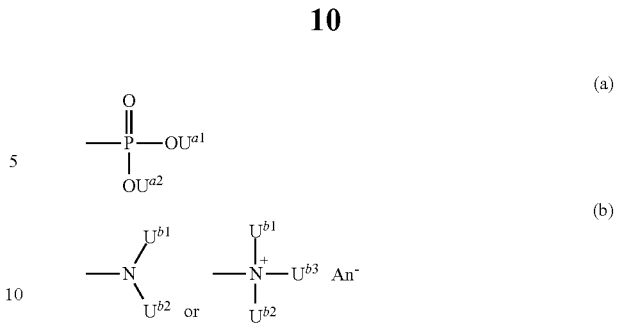

wherein $U^{a1}$, $U^{a2}$, $U^{b1}$, $U^{b2}$ and $U^{b3}$ each independently represent a hydrogen atom or a linear or branched alkyl group having 1 to 5 carbon atoms; $An^-$ represents an anion selected from the group consisting of a halide ion, an inorganic acid ion, a hydroxide ion and an isothiocyanate ion.

In addition, the copolymer according to the coating agent for a flow passage of the present invention may further contain a recurring unit which contains an organic group of the following formula (c):

$$—R^c \quad (c)$$

wherein $R^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, in which the above-mentioned aryl portion may be substituted by a linear or branched alkyl group having 1 to 5 carbon atoms which may be substituted by a halogen atom.

The copolymer according to the coating agent for a flow passage of the present invention has no particular limitation as long as it is a copolymer comprising the recurring unit which contains an organic group of the above-mentioned formula (a), the recurring unit which contains an organic group of the above-mentioned formula (b), and, if necessary, a recurring unit which contains an organic group of the above-mentioned formula (c). In the present invention, the recurring unit which contains an organic group of the above-mentioned formula (c) is different from the recurring unit which contains an organic group of the above-mentioned formula (a) and the recurring unit which contains an organic group of the above-mentioned formula (b). The polymer is preferably a material obtained by radical polymerizing a monomer containing an organic group of the above-mentioned formula (a), a monomer containing an organic group of the above-mentioned formula (b), and, if necessary, a monomer containing an organic group of the above-mentioned formula (c), but a material obtained by polycondensation or polyaddition reaction may be used. Examples of the copolymer may include a vinyl polymerized polymer in which olefin is reacted, a polyamide, a polyester, a polycarbonate and a polyurethane, etc., and among these, a vinyl polymerized polymer in which olefin is reacted or a (meth)acrylic polymer in which a (meth) acrylate compound is polymerized is particularly desired.

A ratio of the recurring unit which contains an organic group of the formula (a) in the copolymer according to the present invention is 3 mol % to 80 mol %. Incidentally, the copolymer according to the present invention may contain two or more kinds of the recurring units which contain an organic group of the formula (a).

A ratio of the recurring unit which contains an organic group of the formula (b) in the copolymer according to the present invention is 3 mol % to 80 mol %. Incidentally, the copolymer according to the present invention may contain two or more kinds of the recurring units which contain an organic group of the formula (b).

A ratio of the recurring unit which contains an organic group of the formula (c) in the copolymer according to the present invention may be the remainder subtracting the ratios of the above-mentioned formulae (a) and (b) from the whole of the copolymer, and, for example, it is 0 mol % to 90 mol %. Incidentally, the copolymer according to the present invention may contain two or more kinds of the recurring units which contain an organic group of the formula (c).

The coating agent for a flow passage of the present invention may contain a solvent. The solvent to be contained in the coating agent for a flow passage of the present invention may be mentioned water, a phosphate buffered physiological saline (PBS) and an alcohol. The alcohol may be mentioned an alcohol having 2 to 6 carbon atoms, for example, ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol (=neopentyl alcohol), 2-methyl-1-propanol, 2-methyl-1-butanol, 2-methyl-2-butanol (=t-amyl alcohol), 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol and cyclohexanol, which may be used singly or a mixed solvent of these in combination, and in the viewpoint of dissolution of the copolymer, it is preferably selected from water, PBS, ethanol, propanol and a mixed solvent thereof, more preferably selected from water, ethanol and a mixed solvent thereof.

Accordingly, the present invention relates to a coating agent for a flow passage containing a copolymer which comprises (i) a recurring unit which contains an organic group of the above-mentioned formula (a), a recurring unit which contains an organic group of the above-mentioned formula (b), and, if necessary, a recurring unit which contains an organic group of the above-mentioned formula (c), and optionally (ii) a solvent. Specific examples of the copolymer and the solvent are as mentioned above.

A concentration of the solid component in the coating agent for a flow passage according to the present invention is desirably 0.01 to 50% by mass to form a coating film uniformly. Also, the concentration of the copolymer in the coating agent for a flow passage is preferably 0.01 to 4% by mass, more preferably 0.01 to 3% by mass, particularly preferably 0.01 to 2% by mass, further preferably 0.01 to 1% by mass. If the concentration of the copolymer is less than 0.01% by mass, the concentration of the copolymer in the coating agent for a flow passage is too low so that a coating film having a sufficient film thickness cannot be formed, while if it exceeds 4% by mass, storage stability of the coating agent for a flow passage is poor, and there is a possibility of causing deposition of the dissolved material or gelation thereof.

Further, to the coating agent for a flow passage of the present invention may be added other substances within the range which does not impair the performance of the obtainable coating film depending on the necessity, in addition to the above-mentioned copolymer and the solvent. The other substances may be mentioned an antiseptic, a surfactant, a primer which heightens adhesiveness with the substrate, an antifungal agent and a saccharide, etc.

To control ion balance of the copolymer in the coating agent for a flow passage according to the present invention, a process of previously adjusting a pH of the coating agent for a flow passage may be further contained. The pH adjustment may be carried out, for example, by adding a pH adjusting agent to the composition containing the above-mentioned copolymer and the solvent, to make the pH of the composition 3.5 to 8.5, more preferably 4.0 to 8.0. A kind of the pH adjusting agent which can be used and an amount thereof are optionally selected depending on the concentration of the above-mentioned copolymer, and an existing ratio of the anion and the cation, etc.

Examples of the pH adjusting agent may include an organic amine such as ammonia, diethanolamine, pyridine, N-methyl-D-glucamine, tris(hydroxymethyl)-aminomethane, etc.; an alkali metal hydroxide such as potassium hydroxide, sodium hydroxide, etc.; an alkali metal halide such as potassium chloride, sodium chloride, etc.; an inorganic acid such as sulfuric acid, phosphoric acid, hydrochloric acid, carbonic acid, etc., or an alkali metal salt thereof; a quaternary ammonium cation such as choline, etc., or a mixture thereof (for example, a buffer such as a phosphate buffered physiological saline, etc.). Among these, ammonia, diethanolamine, sodium hydroxide, choline, N-methyl-D-glucamine and tris(hydroxymethyl)aminomethane are preferred, and ammonia, diethanolamine, sodium hydroxide and choline are particularly preferred.

Accordingly, the present invention relates to the coating agent for a flow passage which comprises (i) the copolymer containing the recurring unit which contains an organic group of the above-mentioned formula (a), the recurring unit which contains an organic group of the above-mentioned formula (b) and, if necessary, the recurring unit which contains an organic group of the above-mentioned formula (c), and optionally (ii) the solvent, and/or (iii) the pH adjusting agent. Specific examples of the copolymer, the solvent and the pH adjusting agent are as mentioned above.

The copolymer contained in the coating agent for a flow passage of the present invention particularly preferably used is a copolymer comprising recurring units of the following formulae (a1) and (b1).

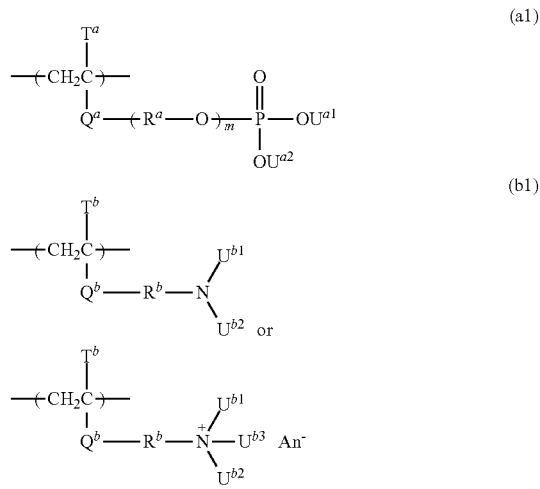

In the formulae, $T^a$ and $T^b$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom, $U^{a1}$, $U^{a2}$, $U^{b1}$, $U^{b2}$ and $U^{b3}$ each independently represent a hydrogen atom or a linear or branched alkyl group having 1 to 5 carbon atoms, $An^-$ represents an anion selected from the group consisting of a halide ion, an inorganic acid ion, a hydroxide ion and an isothiocyanate ion, and m represents an integer of 0 to 6.

The copolymer contained in the coating agent for a flow passage of the present invention may further contain a recurring unit of the following formula (c1):

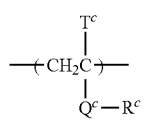

(c1)

In the formula, $T^c$ each independently represent a hydrogen atom or a linear or branched alkyl group having 1 to 5 carbon atoms, $Q^c$ represents a single bond, an ether bond or an ester bond, $R^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, in which the above-mentioned aryl portion may be substituted by a linear or branched alkyl group having 1 to 5 carbon atoms which may be substituted by a halogen atom.

In the formula (a1), m is an integer of 0 to 6, preferably an integer of 1 to 6, more preferably an integer of 1 to 5, and particularly preferably 1.

A ratio of the recurring unit of the formula (a1) contained in the copolymer according to the present invention is 3 mol % to 80 mol %. Incidentally, the copolymer according to the present invention may contain two or more kinds of the recurring units of the formula (a1).

A ratio of the recurring unit of the formula (b1) contained in the copolymer according to the present invention is 3 mol % to 80 mol %. Incidentally, the copolymer according to the present invention may contain two or more kinds of the recurring units of the formula (b1).

A ratio of the recurring unit of the formula (c1) contained in the copolymer according to the present invention may be the remainder subtracting the ratios of the above-mentioned formula (a1) and the formula (b1) from the whole of the copolymer, and is, for example, 0 mol % to 90 mol %. Incidentally, the copolymer according to the present invention may contain two or more kinds of the recurring units of the formula (c1).

The copolymer contained in the coating agent for a flow passage of the present invention may also be a copolymer obtainable by reacting (polymerizing) a monomer mixture containing compounds of the following formulae (A) and (B):

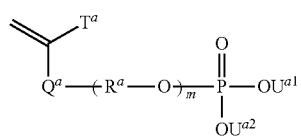

(A)

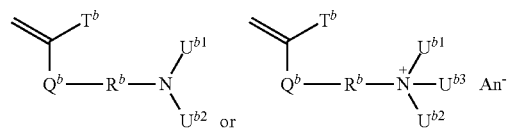

(B)

wherein
$T^a$ and $T^b$ each independently represent a hydrogen atom or a linear or branched alkyl group having 1 to 5 carbon atoms; $Q^a$ and $Q^b$ each independently represent a single bond, an ester bond or an amide bond;
$R^a$ and $R^b$ each independently represent a linear or branched alkylene group having 1 to 10 carbon atoms which may be substituted by a halogen atom;
$U^{a1}$, $U^{a2}$, $U^{b1}$, $U^{b2}$ and $U^{b3}$ each independently represent a hydrogen atom or a linear or branched alkyl group having 1 to 5 carbon atoms;
$An^-$ represents an anion selected from the group consisting of a halide ion, an inorganic acid ion, a hydroxide ion and an isothiocyanate ion; and
m represents an integer of 0 to 6,
in a solvent.

The copolymer contained in the coating agent for a flow passage of the present invention may be a copolymer obtainable from a monomer mixture further containing a compound of the following formula (C):

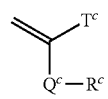

(C)

wherein
$T^c$ each independently represents a hydrogen atom or a linear or branched alkyl group having 1 to 5 carbon atoms;
$Q^c$ represents a single bond, an ether bond or an ester bond; and
$R^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, in which the above-mentioned aryl portion may be substituted by a linear or branched alkyl group having 1 to 5 carbon atoms which may be substituted by a halogen atom.

In the present invention, $T^a$, $T^b$ and $T^c$ are each preferably a hydrogen atom, a methyl group or an ethyl group, more preferably a hydrogen atom or a methyl group. $Q^a$, $Q^b$ and $Q^c$ are each preferably a single bond or an ester bond, more preferably an ester bond. $R^a$ and $R^b$ are each preferably a linear or branched alkylene group having 1 to 5 carbon atoms, more preferably a methylene group, an ethylene group or a propylene group. $R^c$ is preferably a linear or branched alkyl group having 4 to 18 carbon atoms or a cycloalkyl group having 3 to 10 carbon atoms, and more preferably a butyl group, a pentyl group, a hexyl group or an isomer thereof, or a cyclohexyl group. $U^{a1}$, $U^{a2}$, $U^{b1}$, $U^{b2}$ and $U^{b3}$ are each preferably a hydrogen atom, a methyl group, an ethyl group or a t-butyl group, $U^{a1}$ and $U^{a2}$ of the formula (a) are each more preferably a hydrogen atom, and $U^{b1}$, $U^{b2}$ and $U^{b3}$ of the formula (b) are each more preferably a hydrogen atom, a methyl group, an ethyl group or a t-butyl group.

Specific examples of the above-mentioned formula (A) preferably used may include vinylphosphonic acid, acid phosphoxyethyl (meth)acrylate, 3-chloro-2-acid phosphoxypropyl (meth)acrylate, acid phosphoxypropyl (meth)acrylate, acid phosphoxymethyl (meth)acrylate, acid phosphoxy polyoxyethylene glycol mono(meth)acrylate and acid phosphoxy polyoxypropylene glycol mono(meth)acrylate, etc., and among these, vinylphosphonic acid, acid phosphoxyethyl methacrylate (=phosphoric acid 2-(methacryloyloxy) ethyl) or acid phosphoxy polyoxyethylene glycol monomethacrylate, and most preferred is acid phosphoxyethyl methacrylate (=phosphoric acid 2-(methacryloyloxy) ethyl).

Structural formulae of vinylphosphonic acid, acid phosphoxyethyl methacrylate (=phosphoric acid 2-(methacryloyloxy)ethyl), acid phosphoxy polyoxyethylene glycol monomethacrylate and acid phosphoxy polyoxypropylene glycol monomethacrylate are represented by the following formulae (A-1) to (A-4), respectively.

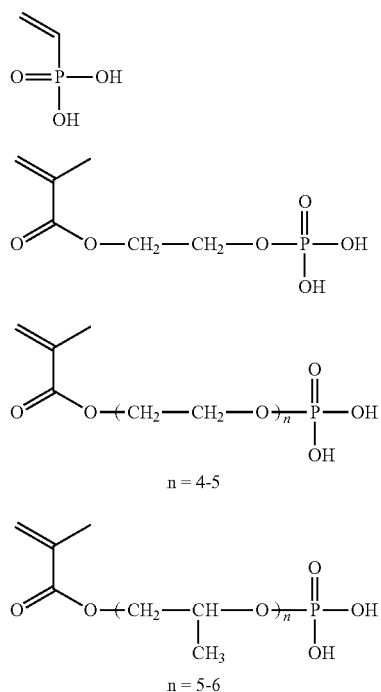

These compounds may contain a (meth)acrylate compound having two functional groups of the formula (D) or (E) mentioned later at the time of synthesis in some cases.

Specific examples of the above-mentioned formula (B) may include dimethylaminoethyl (meth)acrylate, diethylaminoethyl (meth)acrylate, dimethylaminopropyl (meth)acrylate, 2-(t-butylamino)ethyl (meth)acrylate, methacryloylcholine chloride, etc., and among these, dimethylaminoethyl (meth)acrylate, methacryloylcholine chloride or 2-(t-butylamino)ethyl (meth)acrylate is preferably used and dimethylaminoethyl (meth)acrylate is most preferably used.

Structural formulae of dimethylaminoethyl acrylate (=acrylic acid 2-(dimethylamino)ethyl), diethylaminoethyl methacrylate (=methacrylic acid 2-(diethylamino)ethyl), dimethylaminoethyl methacrylate (=methacrylic acid 2-(dimethylamino)ethyl), methacryloylcholine chloride and 2-(t-butylamino)ethyl methacrylate (=methacrylic acid 2-(t-butylamino)ethyl) are shown by the following formulae (B-1) to (B-5), respectively.

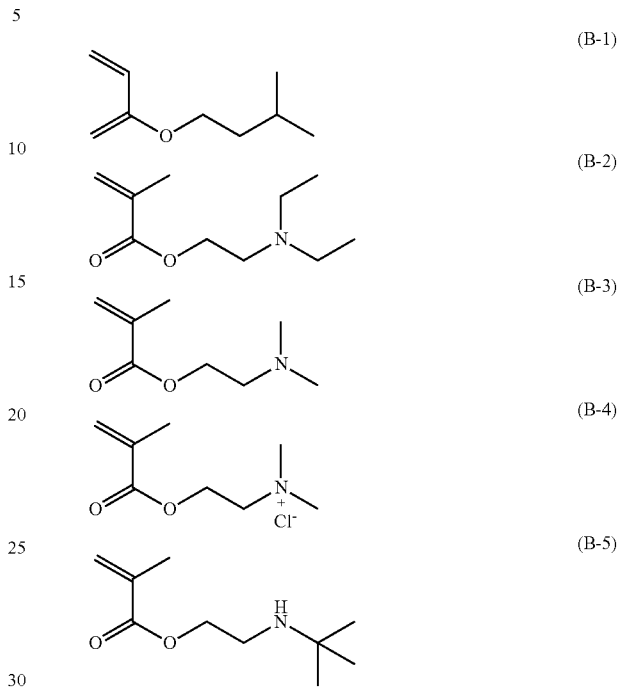

Specific examples of the above-mentioned formula (C) may include a linear or branched alkyl ester of (meth)acrylic acid such as butyl (meth)acrylate, 2-ethylhexyl (meth)acrylate, lauryl (meth)acrylate, stearyl (meth)acrylate, etc.; a cyclic alkyl ester of (meth)acrylic acid such as cyclohexyl (meth)acrylate, isobornyl (meth)acrylate, etc.; an aralkyl ester of (meth)acrylic acid such as benzyl (meth)acrylate, phenethyl (meth)acrylate, etc.; a styrene-based monomer such as styrene, methylstyrene, chloromethylstyrene, etc.; a vinyl ether-based monomer such as methyl vinyl ether, butyl vinyl ether, etc.; and a vinyl ester-based monomer such as vinyl acetate, vinyl propionate, etc. Among these, butyl (meth)acrylate or cyclohexyl (meth)acrylate is preferably used.

Structural formulae of the butyl methacrylate (=methacrylic acid butyl) and cyclohexyl methacrylate (=methacrylic acid cyclohexyl) are represented by the following formulae (C-1) and (C-2), respectively.

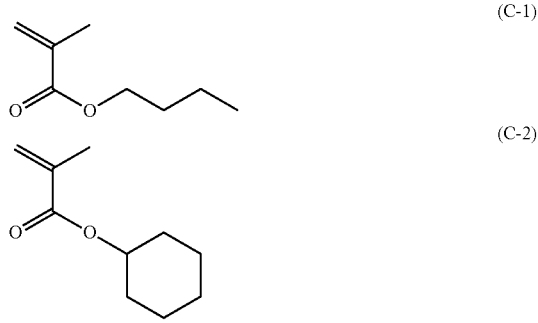

The copolymer according to the present invention may be further copolymerized with an optional fourth component.

As the fourth component, for example, a (meth)acrylate compound having two or more functional groups may be copolymerized, and a part of the polymer may be partially three-dimensionally crosslinked. Such a fourth component may be mentioned, for example, a bifunctional monomer of the following formula (D) or (E):

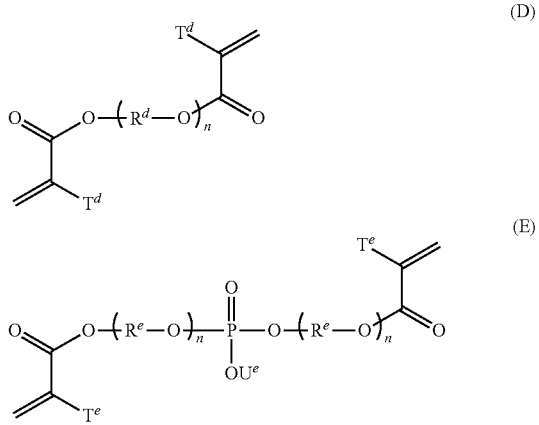

wherein $T^d$, $T^e$ and $U^e$ each independently represent a hydrogen atom or a linear or branched alkyl group having 1 to 5 carbon atoms, $R^d$ and $R^e$ each independently represent a linear or branched alkylene group having 1 to 10 carbon atoms which may be substituted by a halogen atom; and n represents an integer of 1 to 6. That is, the copolymer according to the present invention preferably contains a crosslinked structure derived from such a bifunctional monomer.

In the formulae (D) and (E), $T^d$ and $T^e$ are preferably each independently a hydrogen atom, a methyl group or an ethyl group, more preferably, each independently, a hydrogen atom or a methyl group.

In the formula (E), $U^e$ is preferably a hydrogen atom, a methyl group or an ethyl group, more preferably a hydrogen atom.

In the formula (D), $R^d$ is preferably a linear or branched alkylene group having 1 to 3 carbon atoms which may be substituted by a halogen atom, more preferably, each of which independently represents an ethylene group or a propylene group, or an ethylene group or a propylene group each substituted by one chlorine atom, and particularly preferably an ethylene group or a propylene group. Also, in the formula (D), n preferably represents an integer of 1 to 5, particularly preferably 1.

In the formula (E), $R^e$ is preferably a linear or branched alkylene group having 1 to 3 carbon atoms which may be substituted by a halogen atom, more preferably, each of which independently represents an ethylene group or a propylene group, or an ethylene group or a propylene group each substituted by one chlorine atom, and particularly preferably an ethylene group or a propylene group. Also, in the formula (E), n preferably represents an integer of 1 to 5, particularly preferably 1.

The bifunctional monomer of the formula (D) is preferably mentioned ethylene glycol di(meth)acrylate, triethylene glycol di(meth)acrylate, propylene glycol di(meth)acrylate, or the bifunctional monomer derived from the above-mentioned formula (A-3) or (A-4), etc.

The bifunctional monomer of the formula (E) is preferably mentioned bis(methacryloyloxymethyl) phosphate, bis[(2-methacryloyloxy)ethyl] phosphate, bis[3-(methacryloyloxy)propyl] phosphate, or the bifunctional monomer derived from the above-mentioned formula (A-3) or (A-4).

In addition, as trifunctional (meth)acrylate compound, phosphynylidine tris(oxy-2,1-ethanediyl) triacrylate may be mentioned.

Among these fourth components, particularly preferred are ethylene glycol dimethacrylate, a dimethacrylate having a recurring unit of ethylene glycol or propylene glycol among the bifunctional monomer derived from the above-mentioned formula (A-3) or (A-4), bis[2-(methacryloyloxy)ethyl] phosphate, and a dimethacrylate having a recurring unit of ethylene glycol or propylene glycol via a phosphate group among the bifunctional monomer derived from the above-mentioned formula (A-3) or (A-4). The structural formulae are represented by the following formulae (D-1) to (D-3) and the formulae (E-1) to (E-3), respectively.

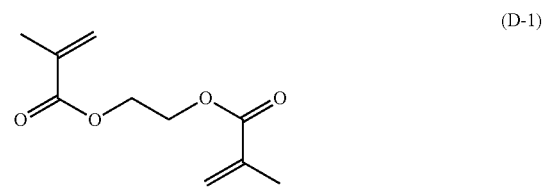

(D-1)

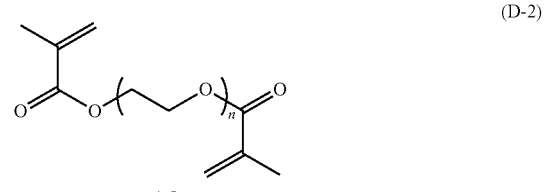

(D-2)

n = 4-5

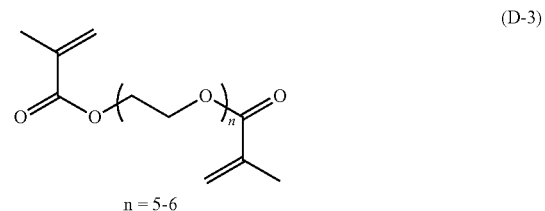

(D-3)

n = 5-6

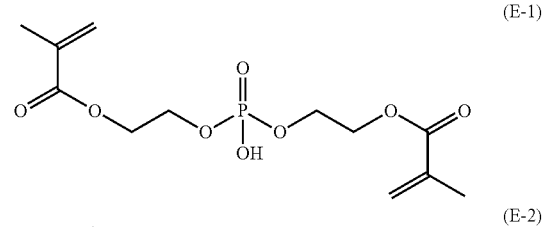

(E-1)

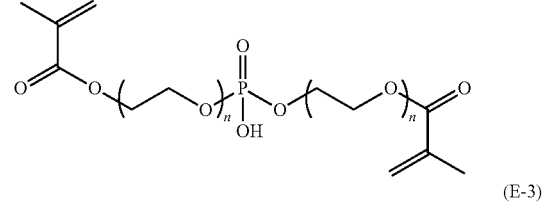

(E-2)

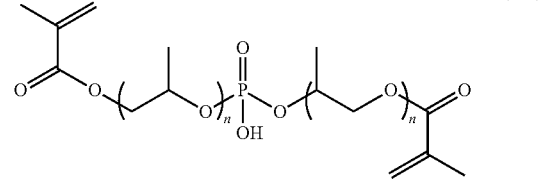

(E-3)

The copolymer may contain one or more kinds of these fourth components.

A ratio of the fourth component in the above-mentioned copolymer, for example, the cross-linked structure derived from the bifunctional monomer of the above-mentioned formula (D) or (E) is 0 mol % to 50 mol %.

A ratio of the compound of the formula (A) based on the whole monomers forming the above-mentioned copolymer is 3 mol % to 80 mol %. In addition, the compound of the formula (A) may be two or more kinds.

A ratio of the compound of the formula (B) based on the whole monomers forming the above-mentioned copolymer is 3 mol % to 80 mol %. In addition, the compound of the formula (B) may be two or more kinds.

A ratio of the compound of the formula (C) based on the whole monomers forming the above-mentioned copolymer may be the remainder subtracting the ratio of the above-mentioned formulae (A) and (B) from the whole monomers, and is, for example, 0 mol % to 90 mol %. In addition, the compound of the formula (C) may be two or more kinds.

As the synthetic method of the copolymer according to the present invention, there may be mentioned the methods of the radical polymerization, the anion polymerization, the cation polymerization, etc., which are general synthetic methods of an acrylic polymer or a methacrylic polymer, etc., whereby a copolymer can be synthesized. As the reaction form thereof, various methods such as the solution polymerization, the suspension polymerization, the emulsion polymerization, the bulk polymerization, etc., may be employed.

The coating agent for a flow passage according to the present invention may be prepared by optionally diluting a desired copolymer with a desired solvent to a predetermined concentration.

Further, the coating agent for a flow passage according to the present invention may be prepared from the varnish containing the copolymer. The varnish containing the copolymer can be prepared by the manufacturing method including a process of reacting (polymerizing) the compounds of the above-mentioned formulae (A) and (B), and if necessary, (C), in a solvent with a total concentration of those compounds of 0.01% by mass to 20% by mass.

The solvent to be used in the polymerization reaction may be water, a phosphate buffered solution or an alcohol such as ethanol, etc., or a mixed solvent in which these solvents are used in combination, and desirably contains water or ethanol. It is more preferred to contain water or ethanol in an amount of 10% by mass or more and 100% by mass or less. It is further preferred to contain water or ethanol in an amount of 50% by mass or more and 100% by mass or less. It is moreover preferred to contain water or ethanol in an amount of 80% by mass or more and 100% by mass or less. It is furthermore preferred to contain water or ethanol in an amount of 90% by mass or more and 100% by mass or less. It is preferred that a total amount of water and ethanol is 100% by mass.

As the reaction concentration, for example, the concentration of the compounds of the above-mentioned formula (A) or the formula (B) in the reaction solvent is preferably 0.01% by mass to 4% by mass. If the concentration is 4% by mass or more, for example, the copolymer is sometimes gelled in the reaction solvent due to strong associative property possessed by the phosphoric acid group of the formula (A). If the concentration is 0.01% by mass or less, the concentration of the obtained varnish is too low, so that it is difficult to prepare the composition for forming a coating film for obtaining a coating film having a sufficient film thickness. The concentration is more preferably 0.01% by mass to 3% by mass and, for example, 3% by mass, 2% by mass or 1% by mass.

Also, in the synthesis of the copolymer according to the present invention, a monomer containing an organic group of the above-mentioned formula (a) and a monomer containing an organic group of the above-mentioned formula (b) are, for example, after making an acidic phosphoric acid ester monomer (a half salt) as shown in the following formula (1), polymerizing, if necessary, with the compound of the formula (C) to prepare the copolymer.

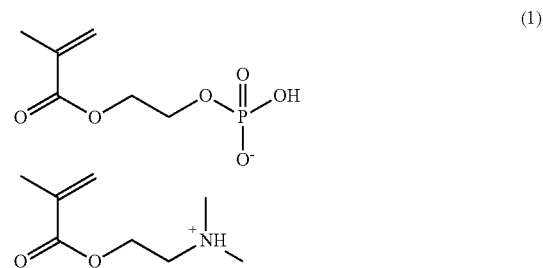

(1)

The phosphate group-containing monomer is a monomer easily associated, so that it may be added dropwise to the reaction solvent little by little so as to rapidly disperse therein when it is added dropwise to the reaction system.

Moreover, the reaction solvent may be heated (for example, 40° C. to 100° C.) to increase the solubility of the monomer and the polymer.

To proceed with the polymerization reaction efficiently, a polymerization initiator is desirably used. Examples of the polymerization initiator to be used may include 2,2'-azobis(isobutyronitrile), 2,2'-azobis(2-methylbutyronitrile), 2,2'-azobis(2,4-dimethylvaleronitrile) (available from Wako Pure Chemical Industries, Ltd., V-065, 10 hour half-life temperature; 51° C.), 4,4'-azobis(4-cyanovaleric acid), 2,2'-azobis(4-methoxy-2,4-dimethylvaleronitrile), 1,1'-azobis(cyclohexane-1-carbonitrile), 1-[(1-cyano-1-methylethyl)azo]formamide, 2,2'-azobis[2-(2-imidazolin-2-yl)propane], 2,2'-azobis(2-methylpropionamidine) dihydrochloride, 2,2'-azobis[2-methyl-N-(2-hydroxyethyl)propionamide] (available from Wako Pure Chemical Industries, Ltd.; VA-086, 10 hour half-life temperature; 86° C.), benzoyl peroxide (BPO), 2,2'-azobis[N-(2-carboxyethyl)-2-methylpropionamidine] n-hydrate (available from Wako Pure Chemical Industries, Ltd.; VA-057, 10 hour half-life temperature; 57° C.), 4,4'-azobis(4-cyanopentanoic acid) (available from Wako Pure Chemical Industries, Ltd.; V-501), 2,2'-azobis[2-(2-imidazolin-2-yl)propane] dihydrochloride (available from Wako Pure Chemical Industries, Ltd.; VA-044, 10 hour half-life temperature; 44° C.), 2,2'-azobis[2-(2-imidazolin-2-yl)propane] disulfate dihydrate (available from Wako Pure Chemical Industries, Ltd.; VA-046B, 10 hour half-life temperature; 46° C.), 2,2'-azobis[2-(2-imidazolin-2-yl)propane] (available from Wako Pure Chemical Industries, Ltd.; VA-061, 10 hour half-life temperature; 61° C.), 2,2'-azobis(2-amidinopropane) dihydrochloride (available from Wako Pure Chemical Industries, Ltd.; V-50, 10 hour half-life temperature; 56° C.), peroxodisulfuric acid or t-butyl hydroperoxide, etc.

When solubility in water, ion balance and an interaction with the monomers are taking into consideration, it is preferred to select the material from 2,2'-azobis[2-methyl-N-(2-hydroxyethyl)propionamide], 2,2'-azobis[N-(2-carboxyethyl)-2-methylpropionamidine] n-hydrate, 4,4'-azobis (4-cyanopentanoic acid), 2,2'-azobis[2-(2-imidazolin-2-yl) propane] dihydrochloride, 2,2'-azobis[2-(2-imidazolin-2-yepropane] disulfate dihydrate, 2,2'-azobis[2-(2-imidazolin-2-yl)propane], 2,2'-azobis(2-amidinopropane) dihydrochloride and peroxodisulfuric acid.

When solubility in an organic solvent, ion balance and an interaction with the monomers are taking into consideration, it is desired to use 2,2'-azobis(2,4-dimethylvaleronitrile) or 2,2'-azobis(isobutyronitrile).

An amount of the polymerization initiator to be added is 0.05% by mass to 10% by mass based on the total weight of the monomers to be used for the polymerization.

As the reaction conditions, the polymerization reaction proceeds by heating a reaction vessel by an oil bath, etc., at 50° C. to 200° C. and stirring for 1 hour to 48 hours, more preferably at 80° C. to 150° C. for 5 hours to 30 hours to obtain the copolymer of the present invention. The reaction atmosphere is preferably a nitrogen atmosphere.

As the reaction procedure, the whole reaction substances are charged in the reaction solvent at the room temperature, and then, the polymerization may be carried out by heating to the above-mentioned temperature, or whole or a part of the mixture of the reaction substances may be added dropwise to the previously heated solvent little by little.

According to the latter reaction procedure, the copolymer of the present invention can be prepared by the manufacturing method comprising a process of adding dropwise a mixture containing the compounds of the above-mentioned formulae (A), (B) and, if necessary, (C), a solvent and a polymerization initiator to the solvent maintained at a temperature higher than the 10 hour half-life temperature of the polymerization initiator, and reacting (polymerizing) the compounds.

A molecular weight of the copolymer according to the present invention may be several thousand to several million or so, preferably 5,000 to 5,000,000. It is more preferably 10,000 to 2,000,000. Also, it may be either of a random copolymer, a block copolymer or a graft copolymer, there is no specific limitation in the copolymerization reaction itself for producing the copolymer, and a conventionally known method synthesized in a solution such as radical polymerization, ion polymerization, or polymerization utilizing photopolymerization, macromer or emulsion polymerization can be used. Depending on the purposes thereof to be used, any one of the copolymers of the present invention may be solely used, or a plural kinds of the copolymers may be used by mixing with optionally changing the ratios thereof.

The flow passage device of the present invention has the above-mentioned coating agent for a flow passage at least part of the inner surface of the flow passage.

The above-mentioned flow passage device is typically a micro flow passage device. Examples of the micro flow passage device may include a microreaction device (more specifically a microreactor or a microplant, etc.); a microanalysis device such as an integrated nucleic acid analysis device, a microelectrophoresis device and a microchromatography device; a micro device for preparing an analytical sample of a mass spectrum and a liquid chromatography, etc.; a physicochemical treatment device used for extraction, membrane separation, dialysis, etc.; a micro flow passage chip such as an environmental analysis chip, a clinical analysis chip, a gene analysis chip (a DNA chip), a protein analysis chip (a proteome chip), a sugar chain chip, a chromatograph chip, a cell analysis chip, a pharmaceutical screening chip, etc. Among these, the micro flow passage chip is preferred. There may be more specifically mentioned a platelet-producing flow passage device disclosed in JP 2014-155471A.

The micro flow passage provided in the above-mentioned device is a portion where a minute amount of a sample (preferably a liquid sample) flows, and a width and depth of the flow passage are not particularly limited, and each is generally about 0.01 µm to 1 mm, preferably 1 µm to 800 µm. The width and depth of the flow passage of the micro flow passage may be the same over the entire length of the flow passage or may be partially different sizes and shapes.

Also, the materials at the inner surface of the flow passage may be the same with or different from the materials of the device, and may be mentioned, for example, glass, metal, a metal containing compound or a semi-metal containing compound, activated charcoal or a resin. The metal may be mentioned a typical metal: (an alkali metal: Li, Na, K, Rb, Cs; an alkaline earth metal: Ca, Sr, Ba, Ra), a magnesium group element: Be, Mg, Zn, Cd, Hg; an aluminum group element: Al, Ga, In; a rare earth element: Y, La, Ce, Pr, Nd, Sm, Eu; a tin group element: Ti, Zr, Sn, Hf, Pb, Th; an iron group element: Fe, Co, Ni; a vanadium group element: V, Nb, Ta, a chromium group element: Cr, Mo, W, U; a manganese group element: Mn, Re; a noble metal: Cu, Ag, Au; a platinum group element: Ru, Rh, Pd, Os, Ir, Pt, etc. The metal containing compound or the semi-metal containing compound may be mentioned, for example, ceramics comprising a metal oxide as a basic component, which are a sintered body baked by a heat treatment at a high temperature, a semiconductor such as silicon, an inorganic solid material including a molded product of an inorganic compound such as a metal oxide or a semi-metal oxide (silicon oxide, alumina, etc.), a metal carbide or a semi-metal carbide, a metal nitride or a semi-metal nitride (silicon nitride, etc.), a metal boride or a semi-metal boride, etc., aluminum, nickel-titanium and stainless (SUS304, SUS316, SUS316L, etc.). Among these, silicon is preferred.

The resin may be either a natural resin or a derivative thereof, or a synthetic resin, and the natural resin or a derivative thereof preferably used may be mentioned cellulose, cellulose triacetate (CTA), nitrocellulose (NC), cellulose to which dextran sulfate has been fixed, etc., while the synthetic resin preferably used may be mentioned polyacrylonitrile (PAN), polyester-based polymer alloy (PEPA), polystyrene (PS), polysulfone (PSF), polyethylene terephthalate (PET), polymethyl methacrylate (PMMA), polyvinyl alcohol (PVA), polyurethane (PU), ethylene vinyl alcohol (EVAL), polyethylene (PE), polyester, polypropylene (PP), polyvinylidene fluoride (PVDF), polyether sulfone (PES), polycarbonate (PC), polyvinyl chloride (PVC), polytetrafluoroethylene (PTFE), ultrahigh molecular weight polyethylene(UHPE), polydimethylsiloxane (PDMS), acrylonitrile-butadiene-styrene resin (ABS), Teflon (Registered Trademark) or various kinds of ion exchange resins, etc.

The material of the inner surface of the flow passage may be of one kind or a combination of two or more kinds. Among these materials, it is preferably glass, silicon, silicon oxide, polystyrene (PS), Teflon (Registered Trademark), cycloolefin polymer (COP) or polydimethylsiloxane (PDMS) alone, or a combination selected from these, and most preferably glass, cycloolefin polymer (COP) or polydimethylsiloxane (PDMS) alone, or a combination selected from these. The coating film of the present invention can be formed by low-temperature drying, so that it can also be applied to resins, etc., having low heat resistance.

The present invention relates to a method for manufacturing a flow passage device having a coating agent for a flow passage on at least part of an inner surface of a flow passage, which comprises a process of contacting the coating agent for a flow passage of the present invention with at least part of the inner surface of the flow passage, as mentioned above. There is no particular limitation on the contact between the coating agent for a flow passage and the inner surface of the flow passage, and a method of dipping the flow passage device in the coating agent for a flow passage or feeding the coating agent for a flow passage to the flow passage is used, and a method of feeding the coating agent for a flow passage to the flow passage is preferred. Feeding the liquid may be carried out, for example, by feeding the coating agent for a flow passage in an amount of 0.01 to 100 times the total volume of the flow passage continuously or dividing into plural times with a syringe, etc. According to this procedure, a flow passage device having the coating agent for a flow passage on at least part of the inner surface of the flow passage, preferably over the whole surface thereof can be manufactured.

In addition, the coating at the inner surface of the flow passage obtained by such a method can be used as a flow passage device, more preferably as a platelet-producing flow passage device after the above-mentioned process of contacting with at least part of an inner surface of the flow passage, preferably after the process of feeding the coating agent for a flow passage to the flow passage, without carrying out the drying process as such, or after washing by using water or a medium (for example, water, a buffer solution, a culture medium, etc.) of a sample to be applied to the flow passage device.

That is, after the above-mentioned process of contacting with at least part of an inner surface of the flow passage, preferably after the process of feeding the coating agent for a flow passage to the flow passage, it can be used as a flow passage device, more preferably a platelet-producing flow passage device without carrying out the drying process as such within 48 hours, preferably within 24 hours, more preferably within 12 hours, further preferably within 6 hours, still more preferably within 3 hours, still further preferably within 1 hour, or after washing by using water or a medium (for example, water, a buffer solution, a medium, etc., particularly preferably a medium (for example, IMDM medium (Iscove's Modified Dulbecco's Medium)) of a sample to be applied to the flow passage device.

The above-mentioned process of contacting with at least part of the inner surface of the flow passage is generally carried out at room temperature (10° C. to 35° C.).

The flow passage device may be applied to a drying process. The drying process is carried out under the atmosphere or under vacuum at a temperature preferably within the range of −200° C. to 200° C. According to the drying process, the solvent in the above-mentioned composition for forming a coating film is removed, and the units of the formula (a) and the formula (b) of the copolymer according to the present invention form ionic bonding to completely fix to the substrate.

The coating can be formed by, for example, the drying at room temperature (10° C. to 35° C., for example, 25° C.), and for forming the coating more rapidly, it may be dried, for example, at 40° C. to 50° C. In addition, a drying process at a very low temperature to low temperature (−200° C. to around −30° C.) by a freeze drying method may be used. Freeze drying is called as freeze vacuum drying, and is a method of removing a solvent under a vacuum state by sublimation by generally cooling a material to be dried with a coolant. A general coolant to be used in the freeze drying may be mentioned a mixed medium of dry ice and methanol (−78° C.), liquid nitrogen (−196° C.), etc.

If the drying temperature is −200° C. or lower, a coolant which is not in general must be used so that it lacks in general versatility, and it takes a long time for drying due to sublimation of the solvent so that the efficiency is bad. If the drying temperature is 200° C. or higher, ionic bonding reaction at the surface of the coating excessively proceeds and the surface loses a hydrophilic property, whereby a function of inhibiting adhesion of a biological substance cannot be exhibited. More preferred drying temperature is 10° C. to 180° C., and further preferred drying temperature is 25° C. to 150° C.

Also, to remove impurities, unreacted monomer, etc., remained in the coating, and further to adjust ion balance of the copolymer in the coating, it may be carried out a process of washing with at least one solvent selected from the group consisting of water and an aqueous solution containing an electrolyte. Washing is desirably washing with flowing water or washing with ultrasonic wave, etc. The above-mentioned water and the aqueous solution containing an electrolyte may be a material heated, for example, within the range of 40° C. to 95° C. The aqueous solution containing an electrolyte is preferably PBS, a physiological saline (a material containing sodium chloride alone), a Dulbecco's phosphate buffered physiological saline, a Tris buffered physiological saline, a HEPES buffered physiological saline and a Veronal buffered physiological saline, and PBS is particularly preferred. After fixation, even when the coating film is washed with water, PBS and an alcohol, etc., it does not elute and is still firmly fixed to the substrate. Even when a biological substance is attached to the formed coating, it can be easily removed thereafter by washing with water, etc., and the inner surface of the flow passage onto which the coating of the present invention has been formed has a function of inhibiting adhesion of a biological substance.

A film thickness of the coating to be provided at the inner surface of the flow passage according to the present invention can be suitably adjusted depending on the width or depth of the flow passage provided to the device, the kind of the sample, etc., which may be substantially uniform over the whole length of the flow passage or may be partially ununiform. It is not particularly limited as long as it does not inhibit flow of the sample, and it is preferably 10 to 1000 Å, more preferably 10 to 500 Å, and most preferably 10 to 300 Å.

EXAMPLES

In the following, the present invention is explained further in detail by referring to Synthetic examples and Examples, Test examples, etc., but the present invention is not limited by these.

A weight average molecular weight shown in the following Synthetic examples is a measurement result by Gel Filtration Chromatography (hereinafter abbreviated to as GFC). The measurement conditions, etc., are as follows.

Apparatus: Prominence (manufactured by Shimadzu Corporation)
GFC column: TSKgel GMPWXL (7.8 mm I.D.×30 cm)×2
Flow rate: 1.0 ml/min
Eluent: Ionic aqueous solution
Column temperature: 40° C.
Detector: RI
Injection concentration: Polymer solid content of 0.1% by mass Injection amount: 100 uL
Calibration curve: Cubic approximate curve
Standard sample: Polyethylene oxide (available from Agilent Technologies Japan, Ltd.)×10 kinds Synthetic Example 1

12.40 g of pure water was added to 6.00 g of acid phosphoxyethyl methacrylate (product name; Phosmer M, available from Uni-Chemical Co., Ltd., a non-volatile component by the dryness method at 100° C. for 1 hour: 91.8%, a mixture of acid phosphoxyethyl methacrylate (44.2% by mass), bis[2-(methacryloyloxy)ethyl] phosphate (28.6% by mass) and other substances (27.2% by mass)) and the mixture was sufficiently dissolved. Then, 12.40 g of ethanol, 4.12 g of 2-(dimethylamino)ethyl methacrylate (available from Tokyo Chemical Industry Co., Ltd.) and 0.10 g of 2,2'-azo(2-methyl-N-(2-hydroxyethyl)propionamide) (product name; VA-086, available from Wako Pure Chemical Industries, Ltd.) were further successively added to the aqueous solution of Phosmer M while maintaining to 20° C. or lower. A mixed liquid containing all of the above-mentioned materials which was sufficiently stirred and became homogeneous was introduced into a dropping funnel. On the other hand, 471.13 g of pure water and 37.20 g of ethanol were charged in a three-necked flask equipped with a cooling tube separately, and the flask was flushed with nitrogen and heated to the reflux temperature while stirring. While maintaining this state, the dropping funnel into which the above-mentioned mixed liquid was introduced was set in the three-necked flask, and the mixed liquid was added dropwise into the boiled liquid of pure water and ethanol over 0.5 hour. After the dropwise addition, the mixture was heated and stirred for 24 hours while maintaining the above environment to obtain 506.05 g of a transparent polymerization liquid with a solid content of about 2% by mass. The weight average molecular weight of the obtained transparent liquid by GFC was about 810,000.

Synthetic Example 2

28.00 g of acid phosphoxyethyl methacrylate (product name; Phosmer M, available from Uni-Chemical Co., Ltd., a non-volatile component by the dryness method at 100° C. for 1 hour: 91.8%, a mixture of acid phosphoxyethyl methacrylate (44.2% by mass), bis[2-(methacryloyloxy)ethyl] phosphate (28.6% by mass) and other substances (27.2% by mass)) was stirred while maintaining to 60° C., and 21.37 g of 2-(dimethylamino)ethyl methacrylate was added dropwise thereto. To the mixture were successively added 133.96 g of pure water, then, 44.65 g of ethanol (available from Tokyo Chemical Industry Co., Ltd.), and 0.25 g of 2,2'-azobis(N-(2-carboxyethyl)-2-methylpropionamidine) n-hydrate (product name; VA-057, available from Wako Pure Chemical Industries, Ltd.) while maintaining the mixture to 20° C. or lower. A mixed liquid containing all of the above-mentioned materials which was sufficiently stirred and became homogeneous was introduced into a dropping funnel. On the other hand, 267.93 g of pure water was charged in a three-necked flask equipped with a cooling tube separately, and the flask was flushed with nitrogen and heated to the reflux temperature while stirring. While maintaining this state, the dropping funnel into which the above-mentioned mixed liquid was introduced was set in the three-necked flask, and the mixed liquid was added dropwise into the boiled liquid of pure water and ethanol over 2 hours. After the dropwise addition, the mixture was heated and stirred for 24 hours while maintaining the above environment to obtain 496.16 g of a copolymer-containing varnish with a solid content of about 9.70% by mass. The weight average molecular weight of the obtained transparent liquid by GFC was about 280,000.

Synthetic Example 3

While cooling 25.00 g of acid phosphoxyethyl methacrylate (product name; Phosmer M, available from Uni-Chemical Co., Ltd., a non-volatile component by the dryness method at 100° C. for 1 hour: 91.8%, a mixture of acid phosphoxyethyl methacrylate (44.2% by mass), bis[2-(methacryloyloxy)ethyl] phosphate(28.6% by mass) and other substances (27.2% by mass)) at 35° C. or lower, 29.95 g of choline (48-50% aqueous solution: available from Tokyo Chemical Industry Co., Ltd.) was added thereto and the mixture was stirred until it became homogeneous. To the mixed liquid were successively added 20.95 g of methacryloylcholine chloride 80% aqueous solution (available from Tokyo Chemical Industry Co., Ltd.), 28.67 g of butyl methacrylate (available from Tokyo Chemical Industry Co., Ltd.), 0.70 g of 2,2'-azobis(2,4-dimethylvaleronitrile) (product name; V-65, available from Wako Pure Chemical Industries, Ltd.) and 110.84 g of ethanol while maintaining the mixture at 35° C. or lower. Further, an aqueous solution in which 0.70 g of 2,2'-azobis(N-(2-carboxyethyl)-2-methylpropionamidine) n-hydrate (product name; VA-057, available from Wako Pure Chemical Industries, Ltd.) had been dissolved in 27.71 g of pure water was added to the above-mentioned solution while maintaining the mixture at 35° C. or lower, and a mixed liquid containing all of the above-mentioned materials which was sufficiently stirred and became homogeneous was introduced into a dropping funnel. On the other hand, 56.81 g of pure water and 131.62 g of ethanol were charged in a three-necked flask equipped with a cooling tube separately, and the flask was flushed with nitrogen and heated to the reflux temperature while stirring. While maintaining this state, the dropping funnel into which the above-mentioned mixed liquid was introduced was set in the three-necked flask, and the mixed liquid was added dropwise into the boiled liquid of pure water and ethanol over 1 hour. After the dropwise addition, the mixture was heated and stirred for 24 hours while maintaining the above environment. By cooling the mixture after 24 hours, 432.97 g of a copolymer-containing varnish with a solid content of about 19.86% by mass was obtained. The weight average molecular weight of the obtained colloid state liquid by GFC was about 8,500.

Example 1

The transparent polymerization liquid having a solid content of about 2% by mass obtained in Synthetic example 1 was used as a coating agent for a flow passage.

Example 2

The platelet-producing flow passage device (this is a device manufactured by laminating a flow passage formed by processing PDMS on a glass plate, and accordingly, the inner surface of the flow passage is PDMS and glass) shown in FIGS. 1A to D was obtained from Dai Nippon Printing Co., Ltd. One mL of the coating agent for a flow passage prepared in Example 1 was poured into a flow passage part 3 from introducing parts 1 and 4 using a syringe (5 mL). Subsequently, 5 mL of an IMDM medium (Iscove's Modified Dulbecco's Medium) was poured into the flow passage part 3 from the introducing parts 1 and 4 using a syringe (50 mL). The obtained platelet-producing flow passage device was used in the next Test example 1.

Test Example 1

[Megakaryocytes Adhesion Experiment]

CD34 positive spinal cord derived megakaryocytes (7 day culture) were adjusted with an EBM medium (IMDM with 15% FBS, 1% GPS, 1 µg/mL of Dox, 50 ng/mL of SCF, 50 ng/mL of TPO, ITS, MTG, Ascorbic Acid) so that the concentration of which became $8 \times 10^5$ cells/ml, and each 125 µL of which was poured from the introducing part 1 into the flow passage device subjected to coating in Example 2 and the flow passage device which was not subjected to coating, respectively.

Figure 2:
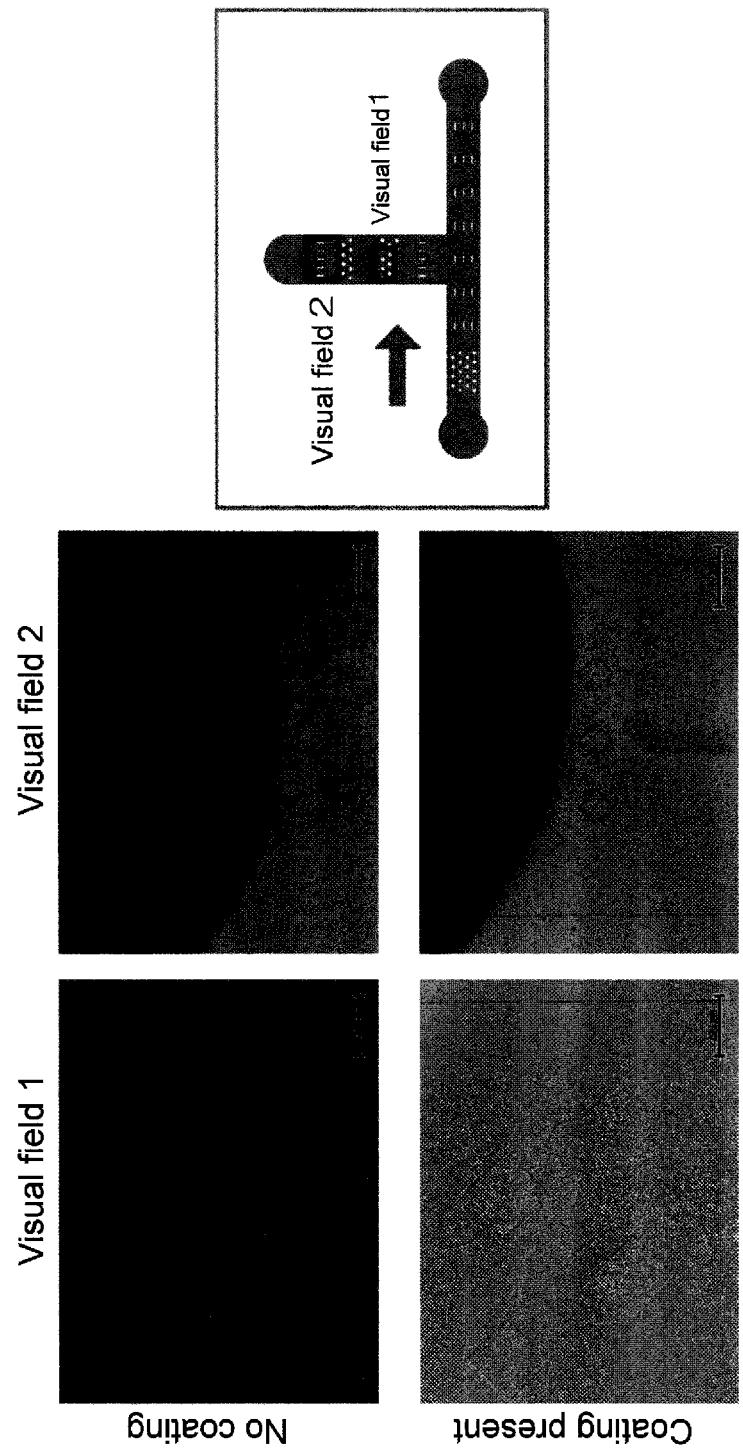
FIG. 2 is results of Test example 1.

Thereafter, the state of the flow passage was observed with a microscope. The results are shown in FIG. 2. The presence or absence of the coating clearly showed a difference in adhesion of megakaryocytes to the flow passage.

Example 3

To 5.00 g of the copolymer-containing varnish obtained in the above-mentioned Synthetic example 2 were added 31.5 g of pure water, 1.35 g of ethanol and 0.24 g of 1 mol/L aqueous sodium hydroxide solution (1N) (available from KANTO CHEMICAL CO., INC.) and the mixture was sufficiently stirred to prepare a coating agent for a flow passage. The pH was 7.3. Into the obtained coating agent were dipped the following mentioned silicon wafer and various kinds of plastic substrates, and these materials were dried in an oven at 45° C. for 24 hours. Thereafter, these materials were sufficiently washed with PBS and pure water to obtain silicon wafer and plastic substrates onto which the coating film has been formed. When the film thickness of the coating film of the silicon wafer was confirmed with an optical interference thickness gauge, it was 90 Å.

(Silicon wafer)

Commercially available silicon wafer for evaluating a semiconductor was used as such.

(Various Kinds of Plastic Substrates) The plastic substrates used are as follows: polyvinyl chloride (PVC), polystyrene petri dish for cell culture (PS petri dish), polystyrene (PS), polyether sulfone (PES), polyethylene terephthalate (PET), polypropylene (PP), polyethylene (PE), quartz glass, two kinds of cycloolefin polymer (COP) sheets (Zeonor (available from ZEON CORPORATION), Zeonex (available from ZEON CORPORATION)), two kinds of polydimethylsiloxane (PDMS) sheets.

Example 4

To 10.00 g of the copolymer-containing varnish obtained in the above-mentioned Synthetic example 3 were added 1.19 g of 1 mol/L hydrochloric acid (1N) (available from KANTO CHEMICAL CO., INC.), 26.78 g of pure water and 62.54 g of ethanol and the mixture was sufficiently stirred to prepare a coating agent for a flow passage. The pH was 3.5. In the same manner as in Example 3, silicon wafer and various kinds of plastic substrates onto which the coating film has been formed were obtained. When the film thickness of the coating film of the silicon wafer was confirmed with an optical interference thickness gauge, it was 112 Å.

Test Example 2

[Evaluation by Static Contact Angle Meter]

Various kinds of plastic substrates on which the coating films obtained in Examples 3 and 4 had been formed were evaluated using a fully automatic contact angle meter (DM-701, Kyowa Interface Science Co., Ltd.). The static contact angle was evaluated by both of measuring the contact angle of water droplets in the atmosphere, and the water contact angle in which various kinds of substrates were placed upside down in water and the contact angle of air bubbles was measured. The measurement results in the atmosphere are shown in Table 1, and the measurement results in water are shown in Table 2.

TABLE 1

| Sample | No coating | Example 3 | Example 4 |
| --- | --- | --- | --- |
| PVC | 89.0 | 74.3 | 88.3 |
| PS (Petri dish) | 85.8 | 85.6 | 71.3 |
| PS | 99.1 | 69.7 | 86.1 |
| PES | 80.5 | 29.6 | 27.7 |
| PET | 84.6 | 67.4 | 87.6 |
| PP | 88.2 | 84.7 | 90.0 |
| PE | 98.4 | 68.0 | 89.8 |
| Quartz | 34.9 | 49.4 | 30.1 |
| Zeonor | 91.7 | 86.9 | 89.9 |
| Zeonex | 99.3 | 87.1 | 73.0 |
| PDMS1 | 114.5 | 106.7 | 109.4 |
| PDMS2 | 108.0 | 105.2 | 104.9 |

TABLE 2

| Sample | No coating | Example 3 | Example 4 |
| --- | --- | --- | --- |
| PVC | 107.3 | 155.6 | 157.9 |
| PS (Petri dish) | 86.9 | 156.8 | 156.4 |
| PS | 92.2 | 154.4 | 156.2 |
| PES | 112.3 | 157.2 | 154.9 |
| PET | 114.6 | 149.1 | 157.9 |
| PP | 82.6 | 155.9 | 157.3 |
| PE | 91.4 | 154.2 | 155.5 |
| Quartz | 141.4 | 159.1 | 159.1 |
| Zeonor | 91.2 | 153.7 | 158.7 |
| Zeonex | 87.0 | 156.4 | 157.4 |
| PDMS1 | 112.4 | 157.2 | 158.7 |
| PDMS2 | 85.5 | 156.1 | 156.4 |

From the measurement results in the atmosphere, no significant difference was found between the contact angles of various kinds of plastic substrates on which the coating film had been formed by the coating agent for a flow passage as compared with the cases without coating. That is, behaviors such as hydrophilization of various kinds of plastics could not be confirmed by coating. On the other hand, from the measurement results in water, the contact angles of various kinds of plastic substrate on which the coating film had been formed by the coating agent for a flow passage were remarkably hydrophilized as compared with the cases without coating. This indicates that a coating for a flow passage is formed on various kinds of plastic substrates.

Example 5

A platelet-producing flow passage device obtained in the same manner as in Example 2 except that the coating agent for a flow passage of Example 2 had been replaced with the coating agent for a flow passage of Example 4 was used in the following Test example 3.

Test Example 3

[Megakaryocytes Adhesion Experiment]

Figure 3:
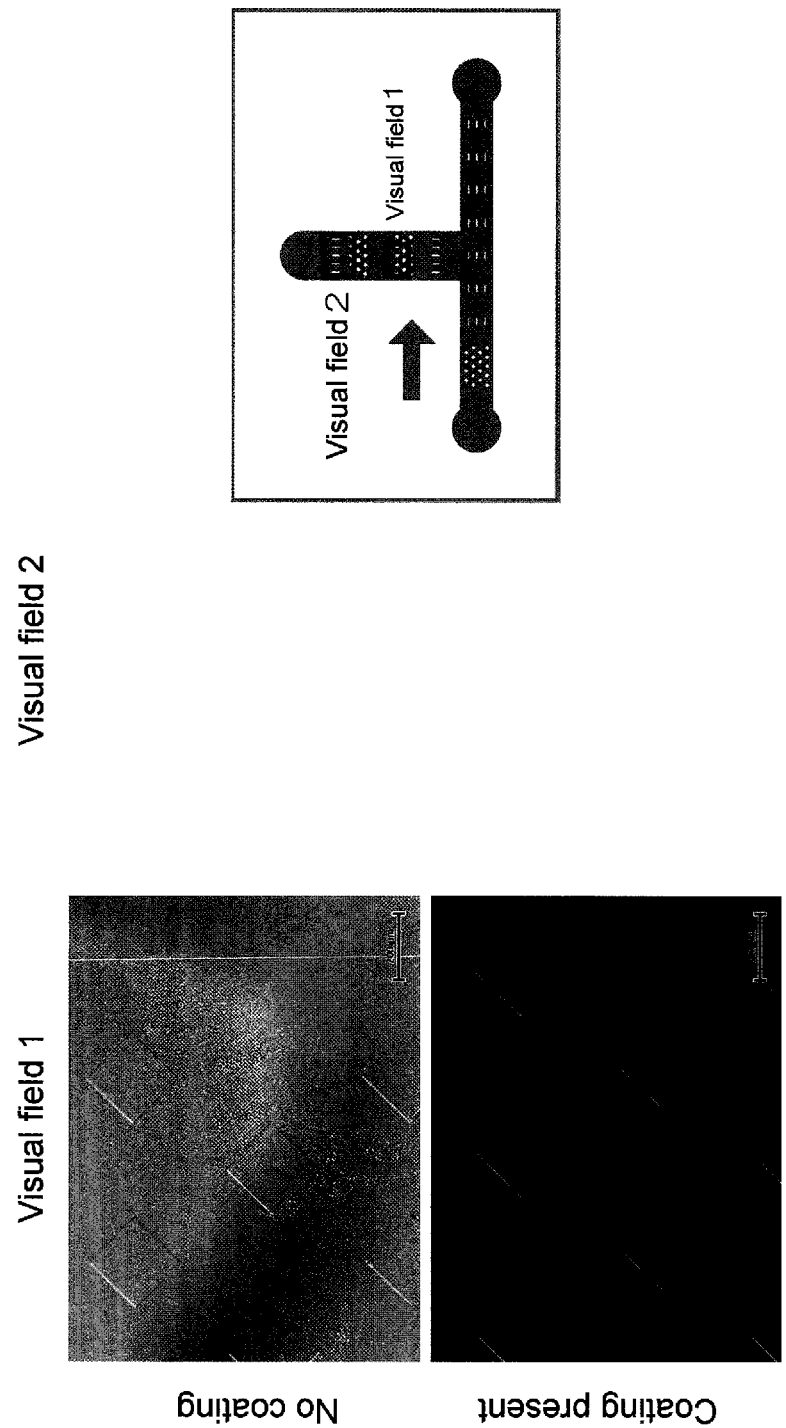
FIG. 3 is results of Test example 3.

In Test example 1, the flow passage device to which coating has been carried out in Example 5 was used instead of the flow passage device to which coating has been carried out in Example 2. The state of the flow passage was observed with a microscope. The results are shown in FIG. 3. The presence or absence of the coating clearly showed a difference in adhesion of megakaryocytes to the flow passage.

UTILIZABILITY IN INDUSTRY

The coating agent for a flow passage of the present invention contains a polymer having an ability to inhibit adhesion of a biological substance, particularly a copolymer containing a specific anion structure and a specific cation structure, which has an excellent ability to inhibit adhesion of a biological substance, and is capable of providing a coating with a simple and easy operation to various kinds of resins such as COP, PDMS, etc. In particular, the coating agent for a flow passage of the present invention can form a coating on the inner surface of the flow passage by an extremely simple and easy operation of feeding the coating agent for a flow passage to a flow passage of a flow passage device, so that it is useful in the point that a desired coating can be applied to the flow passage of the flow passage device after forming the flow passage thereof. Further, the coating formed by the coating agent for a flow passage of the present invention can impart remarkable hydrophilicity in water as well as an ability to inhibit adhesion of a biological substance to the surface of the substrate such as various kinds of resins, etc., including COP, PDMS, etc., so that it is extremely useful as a coating agent for a flow passage of a device using a hydrophilic biological sample.

EXPLANATION OF REFERENCE NUMERALS

1 Introducing part, 2 Main filter part, 3 Flow passage part, 4 Culture medium introducing part, 5 Recovery part, 6 Flow passage part, 7 Glass, 8 PDMS, 9 Slit

The invention claimed is:

1. A coating agent for a flow passage which comprises a (meth)acrylic copolymer comprising a recurring unit which contains an organic group of formula (a1) and a recurring unit which contains an organic group of formula (b1):

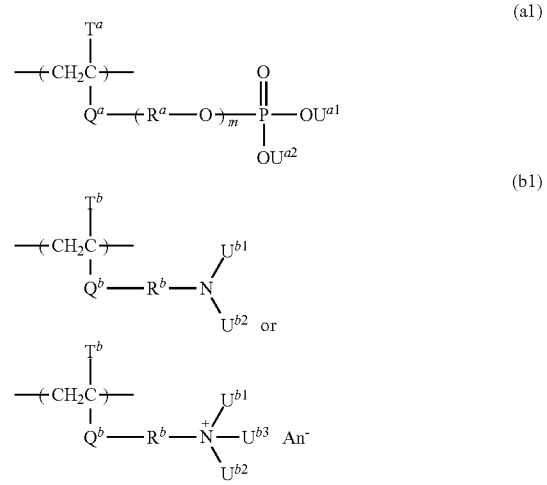

wherein
$T^a$ and $T^b$ each independently represent a hydrogen atom or a methyl group;
$Q^a$ and $Q^b$ each independently represent an ester bond;
$R^a$ and $R^b$ each independently represent a linear or branched alkylene group having 1 to 10 carbon atoms which may be substituted by a halogen atom;
$U^{a1}$, $U^{a2}$, $U^{b1}$, $U^{b2}$ and $U^{b3}$ each independently represent a hydrogen atom or a linear or branched alkyl group having 1 to 5 carbon atoms;
$An^-$ represents an anion selected from the group consisting of a halide ion, an inorganic acid ion, a hydroxide ion and an isothiocyanate ion; and
m represents an integer of 0 to 6; and
wherein the (meth)acrylic copolymer contains the recurring unit which contains the organic group of the formula (a) in an amount from 3 mol % to 80 mol %.

2. The coating agent for a flow passage according to claim 1, wherein the (meth)acrylic copolymer further comprises a recurring unit which contains an organic group of formula (c):

wherein $R^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, where the above-mentioned aryl portion may be substituted by a linear or branched alkyl group having 1 to 5 carbon atoms which may be substituted by a halogen atom.

3. The coating agent for a flow passage according to claim 2, wherein the (meth)acrylic copolymer further comprises a recurring unit of formula (c1):

wherein
$T^c$ represents a hydrogen atom or a methyl group;
$Q^c$ represents a single bond, an ether bond or an ester bond; and
$R^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, where the above-mentioned aryl portion may be substituted by a linear or branched alkyl group having 1 to 5 carbon atoms which may be substituted by a halogen atom.

4. A flow passage device having the coating agent for a flow passage according to claim 1 on at least part of an inner surface of a flow passage.

5. A platelet-producing flow passage device having the coating agent for a flow passage according to claim 1 on at least part of an inner surface of a flow passage.

6. A method for manufacturing a flow passage device having a coating agent for a flow passage on at least part of an inner surface of a flow passage, which comprises a process of contacting the coating agent for a flow passage according to claim 1 with at least part of an inner surface of the flow passage.

7. A method for manufacturing a platelet-producing flow passage device having a coating agent for a flow passage on at least part of an inner surface of a flow passage, which comprises a process of contacting the coating agent for a flow passage according to claim 1 with at least part of an inner surface of the flow passage.

8. The method for manufacturing a flow passage device of claim 6, wherein the coating agent has an ability to inhibit adhesion of a biological substance with at least part of an inner surface of the flow passage after forming the flow passage.

9. The method for manufacturing a platelet-producing flow passage device of claim 7, wherein the coating agent has an ability to inhibit adhesion of a biological substance with at least part of an inner surface of the flow passage after forming the flow passage.

10. A flow passage device having a coating agent for a flow passage on at least part of an inner surface of a flow passage, obtained by a process of feeding the coating agent for a flow passage to the flow passage,
wherein the coating agent for a flow passage comprises a (meth)acrylic copolymer comprising a recurring unit which contains an organic group of formula (a1) and a recurring unit which contains an organic group of formula (b1):

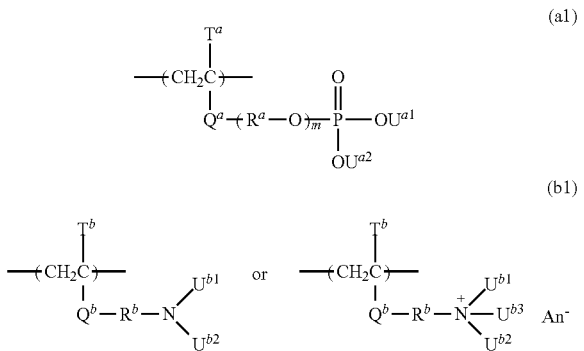

wherein
$T^a$ and $T^b$ each independently represent a hydrogen atom or a methyl group;
$Q^a$ and $Q^b$ each independently represent an ester bond;
$R^a$ and $R^b$ each independently represent a linear or branched alkylene group having 1 to 10 carbon atoms which may be substituted by a halogen atom;
$U^{a1}$, $U^{a2}$, $U^{b1}$, $U^{b2}$ and $U^{b3}$ each independently represent a hydrogen atom or a linear or branched alkyl group having 1 to 5 carbon atoms;
$An^-$ represents an anion selected from the group consisting of a halide ion, an inorganic acid ion, a hydroxide ion and an isothiocyanate ion; and
m represents an integer of 0 to 6; and
wherein the (meth)acrylic copolymer contains the recurring unit which contains the organic group of the formula (a) in an amount from 3 mol % to 80 mol %.

11. The flow passage device according to claim 10, wherein the (meth)acrylic copolymer further comprises a recurring unit which contains an organic group of formula (c):

—R$^c$ (C)

wherein R$^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, where the above-mentioned aryl portion may be substituted by a linear or branched alkyl group having 1 to 5 carbon atoms which may be substituted by a halogen atom.

12. The flow passage device according to claim 10, wherein the (meth)acrylic copolymer further comprises a recurring unit of formula (c1):

wherein
$T^c$ represents a hydrogen atom or a methyl group;
$Q^c$ represents a single bond, an ether bond or an ester bond; and
$R^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, where the above-mentioned aryl portion may be substituted by a linear or branched alkyl group having 1 to 5 carbon atoms which may be substituted by a halogen atom.

13. The flow passage device according to claim 10, which is a platelet-producing flow passage device.

14. A method of forming a coating with a coating agent which comprises applying the coating agent to a flow passage, such that the coating agent fixes to at least part of an inner surface of the flow passage via ionic bonding, wherein the coating agent comprises a (meth)acrylic copolymer comprising a recurring unit which contains an organic group of formula (a) and a recurring unit which contains an organic group of formula (b):

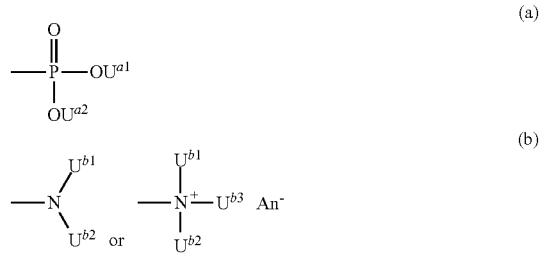

wherein $U^{a1}$, $U^{a2}$, $U^{b1}$, $U^{b2}$ and $U^{b3}$ each independently represent a hydrogen atom or a linear or branched alkyl group having 1 to 5 carbon atoms, and $An^-$ represents an anion selected from the group consisting of a halide ion, an inorganic acid ion, a hydroxide ion and an isothiocyanate ion, and
wherein the (meth)acrylic copolymer contains the recurring unit which contains the organic group of the formula (a) in an amount from 3 mol % to 80 mol %.

15. The method according to claim 14, wherein the (meth)acrylic copolymer further comprises a recurring unit which contains an organic group of formula (c):

—R$^c$ (C)

wherein $R^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, where the above-mentioned aryl portion may be substituted by a linear or branched alkyl group having 1 to 5 carbon atoms which may be substituted by a halogen atom.

16. The method according to claim 14, wherein the (meth)acrylic copolymer comprises recurring units of formulae (a1) and (b1):

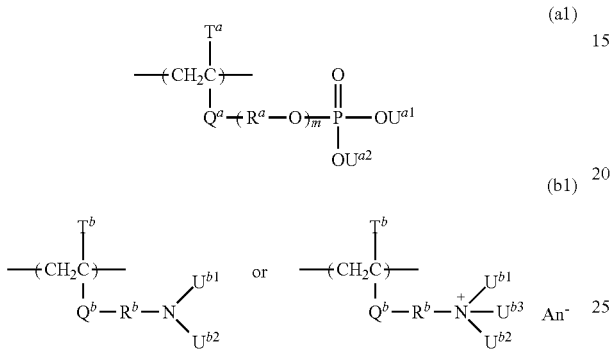

wherein
$T^a$ and $T^b$ each independently represent a hydrogen atom or a methyl group;
$Q^a$ and $Q^b$ each independently represent an ester bond;
$R^a$ and $R^b$ each independently represent a linear or branched alkylene group having 1 to 10 carbon atoms which may be substituted by a halogen atom;
$U^{a1}$, $U^{a2}$, $U^{b1}$, $U^{b2}$ and $U^{b3}$ each independently represent a hydrogen atom or a linear or branched alkyl group having 1 to 5 carbon atoms;
$An^-$ represents an anion selected from the group consisting of a halide ion, an inorganic acid ion, a hydroxide ion and an isothiocyanate ion; and
m represents an integer of 0 to 6.

17. The method according to claim 14, wherein the (meth)acrylic copolymer further comprises a recurring unit of formula (c1):

wherein
$T^c$ represents a hydrogen atom or a methyl group;
$Q^c$ represents a single bond, an ether bond or an ester bond; and
$R^c$ represents a linear or branched alkyl group having 1 to 18 carbon atoms, a cyclic hydrocarbyl group having 3 to 10 carbon atoms, an aryl group having 6 to 10 carbon atoms, an aralkyl group having 7 to 15 carbon atoms or an aryloxyalkyl group having 7 to 15 carbon atoms, where the above-mentioned aryl portion may be substituted by a linear or branched alkyl group having 1 to 5 carbon atoms which may be substituted by a halogen atom.

18. The method according to claim 14, wherein the flow passage is in a platelet-producing flow passage device.

* * * * *